US011767567B2

(12) United States Patent
Fiss et al.

(10) Patent No.: US 11,767,567 B2
(45) Date of Patent: *Sep. 26, 2023

(54) **COMPOSITIONS AND METHODS FOR DETECTION OF *BABESIA***

(71) Applicant: Roche Molecular Systems, Inc., Pleasanton, CA (US)

(72) Inventors: Ellen H. Fiss, Albany, CA (US); Jingtao Sun, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 433 days.

This patent is subject to a terminal disclaimer.

(21) Appl. No.: 16/927,191

(22) Filed: Jul. 13, 2020

(65) Prior Publication Data
US 2020/0399716 A1 Dec. 24, 2020

Related U.S. Application Data

(63) Continuation of application No. 16/031,320, filed on Jul. 10, 2018, now Pat. No. 10,760,137.

(60) Provisional application No. 62/534,046, filed on Jul. 18, 2017.

(51) Int. Cl.
*C07H 21/04* (2006.01)
*C12Q 1/68* (2018.01)
*C12Q 1/6893* (2018.01)

(52) U.S. Cl.
CPC ....... *C12Q 1/6893* (2013.01); *C12Q 2600/16* (2013.01)

(58) Field of Classification Search
None
See application file for complete search history.

(56) References Cited

U.S. PATENT DOCUMENTS 10,760,137 B2 * 9/2020 Fiss ...................... C12Q 1/6893

FOREIGN PATENT DOCUMENTS

EP 0866071 B1 10/2004

* cited by examiner

*Primary Examiner* — Jeanine A Goldberg
(74) *Attorney, Agent, or Firm* — Eric Grant Lee

(57) ABSTRACT

Methods for the rapid detection of the presence or absence of *Babesia* in a biological or non-biological sample are described. The methods can include performing an amplifying step, a hybridizing step, and a detecting step. Furthermore, primers and probes targeting *Babesia* and kits are provided that are designed for the detection of *Babesia*, including, but not limited to, the *Babesia* species of *B. microti, B. divergens, B. duncani,* and *B. venatorum.* Also described are kits, reaction mixtures, and oligonucleotides (e.g., primer and probe) for the amplification and detection of *Babesia.*

5 Claims, 17 Drawing Sheets
Specification includes a Sequence Listing.

A.

B.

A.

B.

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Forward Primer
<220> FEATURE:
<221> NAME/KEY: modified_base
<222> LOCATION: (23)..(23)
<223> OTHER INFORMATION: t-Butyl Benzyl-dA

<400> SEQUENCE: 1
acctgctaaa ttaggatctg gga                                            23

<210> SEQ ID NO 2
<211> LENGTH: 33
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (0)..(1)
<223> OTHER INFORMATION: HEX-Thr
<220> FEATURE:
<221> NAME/KEY: misc_feature
<222> LOCATION: (10)..(11)
<223> OTHER INFORMATION: BHQ-2
<220> FEATURE:
<221> NAME/KEY: misc_feature
<222> LOCATION: (33)..(34)
<223> OTHER INFORMATION: Phosphate

<400> SEQUENCE: 2
ctgttccagt atcgcttctt agagggactt tgc                                 33

<210> SEQ ID NO 3
<211> LENGTH: 24
<212> TYPE: DNA
<213> ORGANISM: Artificial Sequence
<220> FEATURE:
<223> OTHER INFORMATION: Reverse Primer
<220> FEATURE:
<221> NAME/KEY: modified_base
<222> LOCATION: (24)..(24)
<223> OTHER INFORMATION: t-Butyl Benzyl-dC

<400> SEQUENCE: 3
tgttattgcc ttacacttcc ttgc                                           24
```

```
<210> SEQ ID NO 4
<211> LENGTH: 16
<212> TYPE: DNA
<213> ORGANISM: Artificial Sequence
<220> FEATURE:
<223> OTHER INFORMATION: Forward Primer
<220> FEATURE:
<221> NAME/KEY: modified_base
<222> LOCATION: (16)..(16)
<223> OTHER INFORMATION: t-Butyl Benzyl-dA

<400> SEQUENCE: 4
gatgtcctgg gctgca                                                          16

<210> SEQ ID NO 5
<211> LENGTH: 28
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (0)..(1)
<223> OTHER INFORMATION: HEX-Thr
<220> FEATURE:
<221> NAME/KEY: misc_feature
<222> LOCATION: (8)..(9)
<223> OTHER INFORMATION: BHQ-2
<220> FEATURE:
<221> NAME/KEY: misc_feature
<222> LOCATION: (29)..(30)
<223> OTHER INFORMATION: Phosphate

<400> SEQUENCE: 5
aactcgatga atgcatcagt gtagcgcg                                             28

<210> SEQ ID NO 6
<211> LENGTH: 22
<212> TYPE: DNA
<213> ORGANISM: Artificial Sequence
<220> FEATURE:
<223> OTHER INFORMATION: Reverse Primer
<220> FEATURE:
<221> NAME/KEY: modified_base
<222> LOCATION: (22)..(22)
<223> OTHER INFORMATION: t-Butyl Benzyl-dA

<400> SEQUENCE: 6
ccccgtcacg atgcatacta aa                                                   22

<210> SEQ ID NO 7
<211> LENGTH: 22
<212> TYPE: DNA
<213> ORGANISM: Artificial Sequence
<220> FEATURE:
<223> OTHER INFORMATION: Reverse Primer
<220> FEATURE:
<221> NAME/KEY: modified_base
<222> LOCATION: (22)..(22)
<223> OTHER INFORMATION: t-Butyl Benzyl-dA

<400> SEQUENCE: 7
ccccatcacg atgcatacta aa                                                   22

<210> SEQ ID NO 8
<211> LENGTH: 419
<212> TYPE: DNA
<213> ORGANISM: Artificial Sequence
<220> FEATURE:
<223> OTHER INFORMATION: Positive Control
```

```
<400> SEQUENCE: 8
gattagatct aattccacca ggtccagaca tagagaggat tgacagattg atagctcttt      60
cttgattcta tgggtggtgg tgcatggccg ttcttagttg gtggagtgat ttgtctggtt     120
aattccgtta acgaacgaga ccttaacctg ctaaattagg atctgggaca agctttgctg     180
ttccagtatc gcttcttaga gggactttgc gttcataaaa cgcaaggaag tgtaaggcaa     240
taacaggtct gtgatgccct tagatgtcct gggctgcacg cgcgctacac tgatgcattc     300
aacgagtttt tccttggccg tcgggtccgg gtaatcttac agtatgcatc gtgatgggga     360
tagattattg caattattaa tcttgaaaca tgaggattac ccatgtctcg aggtgtaat      419
```

COMPOSITIONS AND METHODS FOR DETECTION OF *BABESIA*

CROSS REFERENCE TO RELATED APPLICATIONS

This application is a Continuation patent application of U.S. patent application Ser. No. 16/031,320, filed Jul. 10, 2018, which claims the benefit of priority of U.S. Provisional Patent Application No. 62/534,046, filed Jul. 18, 2017, both of which are incorporated herein by reference in their entireties.

FIELD OF THE INVENTION

The present disclosure relates to the field of in vitro diagnostics. Within this field, the present invention concerns the amplification and detection of a target nucleic acid that may be present in a sample and particularly, the amplification, detection, and quantitation of a target nucleic acid comprising sequence variations and/or individual mutations of *Babesia* species, using primers and probes. The invention further provides reaction mixtures and kits containing primers and probes for amplification and detection of *Babesia*.

BACKGROUND OF THE INVENTION

*Babesia* (also known as Nuttallia) is a protozoan parasite that infects red blood cells, causing a disease known as babesiosis (also known as piroplasmosis). *Babesia* is usually tick-borne (and tick-transmitted) but is also transmissible by transfusion or from mother to child during pregnancy or delivery.

Most cases of babesiosis are asymptomatic and symptoms, if they occur, are non-specific and may include flu-like symptoms (i.e., fever, chills, sweats, headache, myalgia, and arthralgia), hemolytic anemia, or thrombocytopenia. Babesiosis is particularly life threatening in patients with asplenia, weakened immune systems (e.g., due to cancer lymphoma, or AIDS), co-morbodities, such as liver or kidney disease, or who are over the age of 50. In such patients, multi-organ dysfunction, disseminated intravascular coagulation, and even death, may occur (Vannier, et al., Infect. Dis. Clin. N. Am. 29:357-370 (2015)). *Babesia* parasites reproduce in red blood cells, where they are seen as cross-shaped inclusions and cause hemolytic anemia, not unlike malaria. Due to historical misclassifications, babesiosis has also been known as Texas cattle fever, redwater fever, tick fever, and Nantucket fever. Babesiosis is a malaria-like parasitic disease and is regarded as the second-most common blood parasite of mammals, and has a major impact on the health of domestic animals and humans. Although human babesiosis has historically been uncommon, it is an emerging disease in the Northeastern and Midwestern United States as well as parts of Europe.

*Babesia* is considered to be the second most commonly found blood parasite of mammals (after trypanosomes). More than one hundred species of *Babesia* have been identified. The vast majority of transfusion-associated cases of *Babesia* infection in the U.S. are due to the species *Babesia microti*, and roughly 2% of reported cases are due to *Babesia duncani*. Tick-transmission of *B. microti* mainly occurs in seven states in the Northeast (Connecticut, Maine, Massachusetts, New Hampshire, New Jersey, New York, and Rhode Island) and the upper Midwest (particularly Minnesota and Wisconsin) of the U.S. (see, Herwaldt, et al., Annals of Internal Medicine 155(8):509-520 (2011)). *B. duncani*, is endemic in the West Coast of the U.S. (see, Herwaldt, et al. (2011)). In 2011, there were 1,124 cases of babesiosis reported in the U.S., of which 10 cases were transfusion-associated (see, Center for Disease Control and Prevention: Morbidity and Mortality Weekly Report 61(27): 501-515 (2012)). From 1979-2009, a period spanning 30 years, 162 cases of transfusion-associated babesiosis were reported, at a rate increasing over time (see, Herwaldt, et al. (2011)). Notwithstanding that these statistics may significantly underestimate the true rate of transfusion-associated babesiosis, *Babesia* is the most commonly transmitted transfusion-associated infection (Leiby, Annals of Internal Medicine 155(8):556-557 (2011)). To date, no *Babesia* test for screening blood donors has been licensed, and no pathogen-reduction technologies for *Babesia* are available in the U.S. Although a history of babesiosis infection is a ground for indefinite deferral as a blood donor, many donors may not be aware that they carry the parasite and may have asymptomatic parasitemia and remain infectious for over a year. Further, the *Babesia* parasite is viable in blood products. The majority of transfusion-associated cases are associated with erythrocytes (including leukoreduced or irradiated units), with a few cases due to platelet transfusion. Prospective testing of blood donations in endemic areas of the U.S. has yielded a 0.38% positive rate for *Babesia* (Moritz, et al., N. Engl. J. Med. 375(23):2236-2245 (2016)).

Because no FDA-licensed screening tests are available, to date, the U.S. blood supply is not currently screened for *Babesia*. Accordingly, clinicians may miss the diagnosis of transfusion-associated babesiosis, because the clinical presentation is non-specific, and the nationwide distribution of blood products means that cases can occur outside of areas of high *Babesia* prevalence and outside of peak summer months of tick-borne disease.

Although there are methods (i.e., immunological methods) for detecting *Babesia* in blood and other tissue and/or biological samples, these methods lack sensitivity and do not accurately predict infectivity of *Babesia* in blood. Moreover, such immunological methods cannot detect infection during the period when *Babesia* is present, but has not elicited enough antibodies sufficient for detection. Like other infectious diseases for which blood donations are screened, blood donations must be screened with a sensitive assay to detect *Babesia* so that infected units may be interdicted and discarded.

In the field of molecular diagnostics, the amplification and detection of nucleic acids is of considerable significance. Such methods can be employed to detect any number of microorganisms, such as viruses and bacteria. The most prominent and widely-used amplification technique is the Polymerase Chain Reaction (PCR). Other amplification techniques include Ligase Chain Reaction, Polymerase Ligase Chain Reaction, Gap-LCR, Repair Chain Reaction, 3 SR, NASBA, Strand Displacement Amplification (SDA), Transcription Mediated Amplification (TMA), and Qβ-amplification. Automated systems for PCR-based analysis often make use of a real-time detection of product amplification during the PCR process in the same reaction vessel. Key to such methods is the use of modified oligonucleotides carrying reporter groups or labels.

Thus, rates of *Babesia* infection are dramatically increasing within the U.S., with no reliable sensitive assay or means for its detection in samples. Absent a reliably sensitive means for detecting *Babesia*, the increase in *Babesia* infection rates, in particular, threatens the safety of the blood donor supply. Therefore, there is a need in the art for a quick, reliable, specific, and sensitive method for detecting and quantifying the presence of Babesia in a sample.

SUMMARY OF THE INVENTION

Certain embodiments in the present disclosure relate to methods for the rapid detection of the presence or absence of Babesia in a biological or non-biological sample, for example, multiplex detection and quantitating of Babesia by real-time polymerase chain reaction (PCR) in a single test tube or vessel. Embodiments include methods of detection of Babesia comprising performing at least one cycling step, which may include an amplifying step and a hybridizing step. Furthermore, embodiments include primers, probes, and kits that are designed for the detection of Babesia in a single tube or vessel.

One embodiment of the invention is directed to a method of detecting Babesia in a sample, the method comprising: (a) performing an amplification step comprising contacting the sample with one or more set of primers to produce an amplification product, if a target nucleic acid of Babesia is present in the sample; (b) performing a hybridization step comprising contacting the amplification product, if the target nucleic acid of Babesia is present in the sample, with one or more probes; and (c) detecting the presence or absence of the amplification product, wherein the presence of the amplification product is indicative of the presence of Babesia in the sample, and wherein the absence of the amplification product is indicative of the absence of Babesia in the sample; and wherein the one or more set of primers comprise one or more primers comprising a nucleic sequence of any one of a group consisting of SEQ ID NOs:1, 3, 4, 6, and 7, or a complement thereof; and wherein the one or more probes comprise a nucleic acid sequence of any one of a group consisting of SEQ ID NOs:2 and 5, or a complement thereof. In one embodiment, the Babesia comprises any one or more Babesia species of a group consisting of B. microti, B. divergens, B. duncani, and B. venatorum. In other embodiment, the Babesia species consists of the Babesia species B. microti. In one embodiment, the one or more set of primers comprise a first primer comprising a nucleic acid sequence of SEQ ID NO:1, or a complement thereof, and a second primer comprising a nucleic acid sequence of SEQ ID NO:3, or a complement thereof; and wherein the one or more probes comprise a nucleic acid sequence of SEQ ID NO:2, or a complement thereof. In another embodiment, the Babesia species consists of any one or more of the Babesia species B. divergens, B. duncani, and B. venatorum. In a related embodiment, the one or more set of primers comprise a primer comprising a nucleic acid sequence of SEQ ID NO:4, or a complement thereof, and one or more primers comprising a nucleic acid sequence of any one or more of a group consisting of SEQ ID NOs:6 and 7, or a complement thereof; and wherein the one or more probes comprise a nucleic acid sequence of SEQ ID NO:5, or a complement thereof. In one embodiment, the one or more second primers comprising a nucleic acid sequence of any one or more of a group consisting of SEQ ID NOs:6 and 7, or a complement thereof, comprise a mixture of primers, wherein the mixture of primers comprises: (i) a primer comprising the nucleic acid sequence of SEQ ID NO:6, or a complement thereof, and (ii) a primer comprising the nucleic acid sequence of SEQ ID NO:7, or a complement thereof. In another embodiment, the mixture of primers comprises a mixture with equal amounts of: (i) a primer comprising the nucleic acid sequence of SEQ ID NO:6, or a complement thereof, and (ii) a primer comprising the nucleic acid sequence of SEQ ID NO:7, or a complement thereof. In another embodiment, the Babesia species consists of all of the following Babesia species: B. microti, B. divergens, B. duncani, and B. venatorum. In a related embodiment, the method of detecting B. microti comprises a set of primers for amplification of B. microti, and a probe for hybridizing to the amplification product of B. microti; and wherein the method of detecting B. divergens, B. duncani, and B. venatorum comprises a set of primers for amplification of B. divergens, B. duncani, and B. venatorum, and a probe for hybridization to the amplification products of B. divergens, B. duncani, and B. venatorum. In a related embodiment, (a) the set of primers for amplification of B. microti comprises: (i) a first primer comprising the nucleic acid sequence of SEQ ID NO:1, or a complement thereof and (ii) a second primer comprising the nucleic acid sequence of SEQ ID NO:3, or a complement thereof; and the probe for hybridizing to the amplification product of B. microti comprises the nucleic acid sequence of SEQ ID NO:2, or a complement thereof and (b) the set of primers for amplification of B. divergens, B. duncani, and B. venatorum comprises: (i) a primer comprising the nucleic acid sequence of SEQ ID NO:4, or a complement thereof and (ii) one or more primers comprising a nucleic acid sequence of any one of a group consisting of SEQ ID NOs:6 and 7, or a complement thereof; and the probe for hybridizing to the amplification products of B. divergens, B. duncani, and B. venatorum comprises the nucleic acid sequence of SEQ ID NO:5, or a complement thereof. In another embodiment, the one or more primers comprising a nucleic acid sequence of any one of a group consisting of SEQ ID NOs:6 and 7, or a complement thereof, comprise a mixture of primers, wherein the mixture of primers comprises: (i) a primer comprising the nucleic acid sequence of SEQ ID NO:6, or a complement thereof, and (ii) a primer comprising the nucleic acid sequence of SEQ ID NO:7, or a complement thereof. In a related embodiment, the mixture of primers comprises a mixture with equal amounts of: (i) a primer comprising the nucleic acid sequence of SEQ ID NO:6, or a complement thereof, and (ii) a primer comprising the nucleic acid sequence of SEQ ID NO:7, or a complement thereof. In another embodiment, the sample is a biological sample, such as whole blood, respiratory specimens, urine, fecal specimens, blood specimens, plasma, dermal swabs, nasal swabs, wound swabs, blood cultures, skin, or soft tissue infections. In a related embodiment, the biological sample is whole blood. In another embodiment, the hybridization step comprises contacting the amplification product with the one or more probes, wherein the one or more probes is labeled with a donor fluorescent moiety and a corresponding acceptor moiety; and the detecting step comprises detecting the presence or absence of fluorescent resonance energy transfer (FRET) between the donor fluorescent moiety and the acceptor moiety of the one or more probes, wherein the presence or absence of fluorescence is indicative of the presence or absence of Babesia in the sample. In a related embodiment, the donor fluorescent moiety is HEX or FAM. In another embodiment, the acceptor moiety is a quencher, such as BlackHole Quencher™-2 (BHQ-2). In another embodiment, the donor fluorescent moiety and the acceptor moiety are within 5 to 20 nucleotides of each other. In another embodiment, the donor fluorescent moiety and the acceptor moiety are within 7 to 10 nucleotides of each other. In another embodiment, the donor fluorescent moiety and the acceptor moiety are within 8 nucleotides of each other. In another embodiment, the donor fluorescent moiety and the acceptor moiety are within 10 nucleotides of each other.

Another embodiment of the invention is directed to a method of detecting *Babesia* in a sample, wherein the sample is whole blood, the method comprising: (a) performing an amplification step comprising contacting the sample with one or more set of primers to produce an amplification product, if a target nucleic acid of *Babesia* is present in the whole blood sample; (b) performing a hybridization step comprising contacting the amplification product, if the target nucleic acid of *Babesia* is present in the sample, with one or more probes; and (c) detecting the presence or absence of the amplification product, wherein the presence of the amplification product is indicative of the presence of *Babesia* in the sample, and wherein the absence of the amplification product is indicative of the absence of *Babesia* in the sample; and wherein the one or more set of primers comprises one or more primers comprising a nucleic acid sequence of any one of a group consisting of SEQ ID NOs:1, 3, 4, 6, and 7, or a complement thereof; and wherein the one or more probes comprise a nucleic acid sequence of any one of a group consisting of SEQ ID NOs:2 and 5, or a complement thereof. In another embodiment, the *Babesia* species comprises any one or more *Babesia* species of a group consisting of *B. microti*, *B. divergens*, *B. duncani*, and *B. venatorum*. In another embodiment, the method of detecting *B. microti* comprises a set of primers for amplification of *B. microti*, and a probe for hybridizing to the amplification product of *B. microti*; and wherein the method of detecting *B. divergens*, *B. duncani*, and *B. venatorum* comprises a set of primers for amplification of *B. divergens*, *B. duncani*, and *B. venatorum*, and a probe for hybridization to the amplification products of *B. divergens*, *B. duncani*, and *B. venatorum*. In another embodiment, (a) the set of primers for amplification of *B. microti* comprises: (i) a first primer comprising the nucleic acid sequence of SEQ ID NO:1, or a complement thereof and (ii) a second primer comprising the nucleic acid sequence of SEQ ID NO:3, or a complement thereof; and the probe for hybridizing to the amplification product of *B. microti* comprises the nucleic acid sequence of SEQ ID NO:2, or a complement thereof; and (b) the set of primers for amplification of *B. divergens*, *B. duncani*, and *B. venatorum* comprises: (i) a primer comprising the nucleic acid sequence of SEQ ID NO:4, or a complement thereof; and (ii) one or more primers comprising a nucleic acid sequence of any one of a group consisting of SEQ ID NOs:6 and 7, or a complement thereof; and the probe for hybridizing to the amplification products of *B. divergens*, *B. duncani*, and *B. venatorum* comprises the nucleic acid sequence of SEQ ID NO:5, or a complement thereof. In another embodiment, the one or more primers comprising a nucleic acid sequence of any one or more of a group consisting of SEQ ID NOs:6 and 7, or a complement thereof, comprises a mixture of primers, wherein the mixture of primers comprises: (i) a primer comprising the nucleic acid sequence of SEQ ID NO:6, or a complement thereof, and (ii) a primer comprising the nucleic acid sequence of SEQ ID NO:7, or a complement thereof. In another embodiment, the mixture of primers comprises a mixture with equal amounts of: (i) a primer comprising the nucleic acid sequence of SEQ ID NO:6, or a complement thereof, and (ii) a primer comprising the nucleic acid sequence of SEQ ID NO:7, or a complement thereof.

Another embodiment of the invention is directed to a kit for detecting a nucleic acid of *Babesia* that may be present in a sample, the kit comprising amplification reagents comprising a DNA polymerase, nucleotide monomers, one or more set of primers comprising one or more primers comprising a nucleic acid sequence of any one of a group consisting of SEQ ID NOs:1, 3, 4, 6, and 7, or a complement thereof, and one or more probes comprising a nucleic acid sequence of any one of a group consisting of SEQ ID NOs:2 and 5, or a complement thereof. In another embodiment, the *Babesia* comprises any one or more *Babesia* species of a group consisting of *B. microti*, *B. divergens*, *B. duncani*, and *B. venatorum*. In another embodiment, the kit comprises a set of primers for amplification of *B. microti*, and a probe for hybridizing to the amplification product of *B. microti*; and wherein the kit comprises a set of primers for amplification of *B. divergens*, *B. duncani*, and *B. venatorum*, and a probe for hybridization to the amplification products of *B. divergens*, *B. duncani*, and *B. venatorum*. In another embodiment, (a) the set of primers for amplification of *B. microti* comprises: (i) a first primer comprising the nucleic acid sequence of SEQ ID NO:1, or a complement thereof and (ii) a second primer comprising the nucleic acid sequence of SEQ ID NO:3, or a complement thereof; and the probe for hybridizing to the amplification product of *B. microti* comprises the nucleic acid sequence of SEQ ID NO:2, or a complement thereof; and (b) the set of primers for amplification of *B. divergens*, *B. duncani*, and *B. venatorum* comprises: (i) a primer comprising the nucleic acid sequence of SEQ ID NO:4, or a complement thereof; and (ii) one or more primers comprising a nucleic acid sequence of any one of a group consisting of SEQ ID NOs:6 and 7, or a complement thereof; and the probe for hybridizing to the amplification products of *B. divergens*, *B. duncani*, and *B. venatorum* comprises the nucleic acid sequence of SEQ ID NO:5, or a complement thereof. In another embodiment, the one or more primers comprising a nucleic acid sequence of any one or more of a group consisting of SEQ ID NOs:6 and 7, or a complement thereof, comprises a mixture of primers, wherein the mixture of primers comprises: (i) a primer comprising the nucleic acid sequence of SEQ ID NO:6, or a complement thereof, and (ii) a primer comprising the nucleic acid sequence of SEQ ID NO:7, or a complement thereof. In another embodiment, the mixture of primers comprises a mixture with equal amounts of: (i) a primer comprising the nucleic acid sequence of SEQ ID NO:6, or a complement thereof, and (ii) a primer comprising the nucleic acid sequence of SEQ ID NO:7, or a complement thereof. In another embodiment, the sample is a biological sample, such as whole blood, respiratory specimens, urine, fecal specimens, blood specimens, plasma, dermal swabs, nasal swabs, wound swabs, blood cultures, skin, or soft tissue infections. In another embodiment, the one or more probes comprise a donor fluorescent moiety and a corresponding acceptor moiety. In a related embodiment, the donor moiety is HEX or FAM. In another embodiment, the acceptor moiety is a quencher, such as BlackHole Quencher™-2 (BHQ-2). In another embodiment, the donor fluorescent moiety and the acceptor moiety are within 5 to 20 nucleotides of each other. In another embodiment, the donor fluorescent moiety and the acceptor moiety are within 7 to 10 nucleotides of each other. In another embodiment, the donor fluorescent moiety and the acceptor moiety are within 8 nucleotides of each other. In another embodiment, the donor fluorescent moiety and the acceptor moiety are within 10 nucleotides of each other.

Yet another embodiment of the invention is directed to one or more set of primers and one or more probes for the detection of *Babesia* in a sample, wherein the one or more set of primers comprise one or more primers comprising a nucleic acid sequence of any one of a group selected from SEQ ID NOs:1, 3, 4, 6, and 7, or a complement thereof; and wherein the one or more probes comprise a nucleic acid sequence of any one of a group consisting of SEQ ID NOs:2 and 5, or a complement thereof. In another embodiment, the *Babesia* comprises any one or more *Babesia* species of a group consisting of *B. microti, B. divergens, B. duncani*, and *B. venatorum*. In another embodiment, the one or more set of primers and one or more probes for detecting *B. microti* comprises a set of primers for amplification of *B. microti*, and a probe for hybridizing to the amplification product of *B. microti*; and wherein the one or more set of primers and one or more probes for detecting *B. divergens, B. duncani,* and *B. venatorum* comprises a set of primers for amplification of *B. divergens, B. duncani*, and *B. venatorum*, and a probe for hybridization to the amplification products of *B. divergens, B. duncani,* and *B. venatorum*. In another embodiment, (a) the set of primers for amplification of *B. microti* comprises: (i) a first primer comprising the nucleic acid sequence of SEQ ID NO:1, or a complement thereof; and (ii) a second primer comprising the nucleic acid sequence of SEQ ID NO:3, or a complement thereof; and the one or more probes for hybridizing to the amplification product of *B. microti* comprise the nucleic acid sequence of SEQ ID NO:2, or a complement thereof; and (b) the set of primers for amplification of *B. divergens, B. duncani*, and *B. venatorum* comprises: (i) a primer comprising the nucleic acid sequence of SEQ ID NO:4, or a complement thereof; and (ii) one or more primers comprising a nucleic acid sequence of any one of a group consisting of SEQ ID NOs:6 and 7, or a complement thereof; and the one or more probes for hybridizing to the amplification products of *B. divergens, B. duncani,* and *B. venatorum* comprises the nucleic acid sequence of SEQ ID NO:5, or a complement thereof. In another embodiment, the one or more primers comprising a nucleic acid sequence of any one or more of a group consisting of SEQ ID NOs:6 and 7, or a complement thereof, comprises a mixture of primers, wherein the mixture of primers comprises: (i) a primer comprising the nucleic acid sequence of SEQ ID NO:6, or a complement thereof, and (ii) a primer comprising the nucleic acid sequence of SEQ ID NO:7, or a complement thereof. In another embodiment, the mixture of primers comprises a mixture with equal amounts of: (i) a primer comprising the nucleic acid sequence of SEQ ID NO:6, or a complement thereof, and (ii) a primer comprising the nucleic acid sequence of SEQ ID NO:7, or a complement thereof. In another embodiment, the one or more probes comprise a donor fluorescent moiety and a corresponding acceptor moiety. In a related embodiment, the donor moiety is HEX or FAM. In a another embodiment, the acceptor moiety is a quencher, such as BlackHole Quencher™-2 (BHQ-2). In another embodiment, the donor fluorescent moiety and the acceptor moiety are within 5 to 20 nucleotides of each other. In another embodiment, the donor fluorescent moiety and the acceptor moiety are within 7 to 10 nucleotides of each other. In another embodiment, the donor fluorescent moiety and the acceptor moiety are within 8 nucleotides of each other. In another embodiment, the donor fluorescent moiety and the acceptor moiety are within 10 nucleotides of each other.

Other embodiments provide an oligonucleotide comprising or consisting of a sequence of nucleotides selected from SEQ ID NOs:1-7, or a complement thereof, which oligonucleotide has 100 or fewer nucleotides. In another embodiment, the present disclosure provides an oligonucleotide that includes a nucleic acid having at least 70% sequence identity (e.g., at least 75%, 80%, 85%, 90% or 95%, etc.) to one of SEQ ID NOs:1-5, or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g., 35 or fewer nucleotides, 30 or fewer nucleotides, 25 or fewer nucleotides, 20 or fewer nucleotides, 15 or fewer nucleotides, etc.) In some embodiments, the oligonucleotides comprise at least one modified nucleotide, e.g., to alter nucleic acid hybridization stability relative to unmodified nucleotides. Optionally, the oligonucleotides comprise at least one label and optionally at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill in the art will recognize that individual substitutions, deletions or additions which alter, add or delete a single nucleotide or a small percentage of nucleotides (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the donor fluorescent moiety and the acceptor moiety, e.g., a quencher, may be within no more than 5 to 20 nucleotides (e.g., within 7 or 10 nucleotides) of each other along the length of the probe. In another aspect, the probe includes a nucleic acid sequence that permits secondary structure formation. Such secondary structure formation may result in spatial proximity between the first and second fluorescent moiety. According to this method, the second fluorescent moiety on the probe can be a quencher.

The present disclosure also provides for methods of detecting the presence or absence of *Babesia* or *Babesia* nucleic acid, in a biological sample from an individual. These methods can be employed to detect the presence or absence of *Babesia* nucleic acid in plasma, for use in blood screening and diagnostic testing. Additionally, the same test may be used by someone experienced in the art to assess urine and other sample types to detect and/or quantitate *Babesia* nucleic acid. Such methods generally include performing at least one cycling step, which includes an amplifying step and a dye-binding step. Typically, the amplifying step includes contacting the sample with a plurality of pairs of oligonucleotide primers to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of *Babesia* nucleic acid in the sample, and wherein the absence of binding is indicative of the absence of *Babesia* nucleic acid in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of *Babesia* nucleic acid nucleic acid.

In a further embodiment, a kit for detecting and/or quantitating one or more nucleic acids of Babesia is provided. The kit can include one or more sets of primers specific for amplification of the gene target; and one or more detectable oligonucleotide probes specific for detection of the amplification products.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of Babesia nucleic acid in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Figure 1:
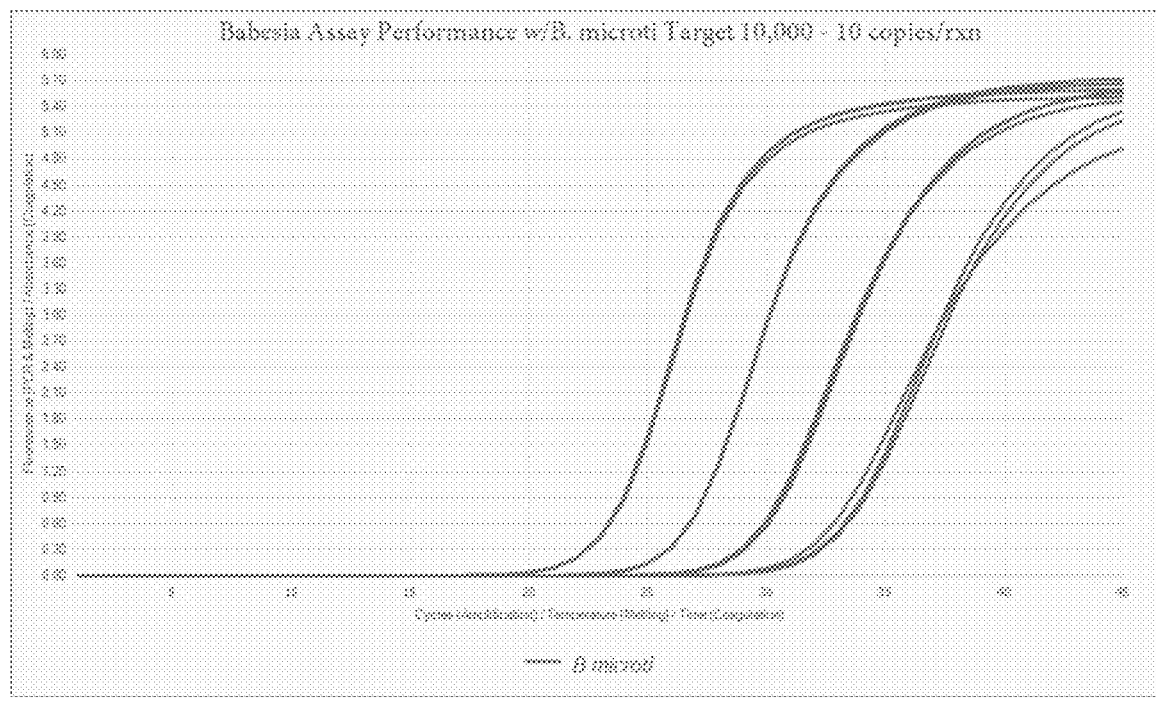
FIG. 1 shows real time PCR growth curves of the *B. microti* nucleic acid test ("395") on pEF113 (*B. microti*) plasmid DNA dilutions (using primers having a nucleic acid sequence of SEQ ID NOs:1 and 3 and a probe having a nucleic acid sequence of SEQ ID NO:2).

Diagnosis of *Babesia* infection by nucleic acid amplification provides a method for rapidly, accurately, reliably, specifically, and sensitively detecting and/or quantitating the *Babesia* infection. A real-time PCR assay for detecting and/or quantitating *Babesia* nucleic acids, including DNA and/or RNA, in a non-biological or biological sample is described herein. Primers and probes for detecting and/or quantitating *Babesia* are provided, as are articles of manufacture or kits containing such primers and probes. The increased specificity and sensitivity of real-time PCR for detection of *Babesia* compared to other methods, as well as the improved features of real-time PCR including sample containment and real-time detection and quantitating of the amplified product, make feasible the implementation of this technology for routine diagnosis of *Babesia* infections in the clinical laboratory. Additionally, this technology may be employed for blood screening as well as for prognosis. This *Babesia* detection assay may also be multiplexed with other assays for the detection of other nucleic acids, e.g., other bacteria and/or viruses, in parallel.

The present disclosure includes oligonucleotide primers and fluorescent labeled hydrolysis probes that hybridize to the *Babesia* genome, in order to specifically identify *Babesia* using, e.g., TaqMan® amplification and detection technology.

The disclosed methods may include performing at least one cycling step that includes amplifying one or more portions of the nucleic acid molecule gene target from a sample using one or more pairs of primers. "*Babesia* primer(s)" as used herein refer to oligonucleotide primers that specifically anneal to nucleic acid sequences found in the *Babesia* genome, and initiate DNA synthesis therefrom under appropriate conditions producing the respective amplification products. Each of the discussed *Babesia* primers anneals to a target such that at least a portion of each amplification product contains nucleic acid sequence corresponding to the target. The one or more amplification products are produced provided that one or more nucleic acid is present in the sample, thus the presence of the one or more amplification products is indicative of the presence of *Babesia* in the sample. The amplification product should contain the nucleic acid sequences that are complementary to one or more detectable probes for *Babesia*. "*Babesia* probe(s)" as used herein refer to oligonucleotide probes that specifically anneal to nucleic acid sequences found in the *Babesia* genome. Each cycling step includes an amplification step, a hybridization step, and a detection step, in which the sample is contacted with the one or more detectable *Babesia* probes for detection of the presence or absence of *Babesia* in the sample.

As used herein, the term "amplifying" refers to the process of synthesizing nucleic acid molecules that are complementary to one or both strands of a template nucleic acid molecule (e.g., nucleic acid molecules from the *Babesia* genome). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group where further "nucleotides" may be attached by a template-dependent DNA polymerase establishing 3' to 5' phosphodiester linkage whereby deoxynucleoside triphosphates are used and whereby pyrophosphate is released.

The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" J. Mol. Biol. 215:403-410, Gish et al. (1993) "Identification of protein coding regions by database similarity search" Nature Genet. 3:266-272, Madden et al. (1996) "Applications of network BLAST server" Meth. Enzymol. 266:131-141, Altschul et al. (1997) "Gapped BLAST and PSI-BLAST: a new generation of protein database search programs" Nucleic Acids Res. 25:3389-3402, and Zhang et al. (1997) "PowerBLAST: A new network BLAST application for interactive or automated sequence analysis and annotation" Genome Res. 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-O-methyl ribo-U, 2'-O-methyl ribo-C, an N4-ethyl-dC, an N6-methyl-dA, a 5-propynyl dU, a 5-propynyl dC, 7-deazadeoxyguanosine (deaza G (u-deaza)) and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features.

Detection/Quantitation of Babesia Target Nucleic Acid

The present disclosure provides methods to detect Babesia by amplifying, for example, a portion of the Babesia nucleic acid sequence. Specifically, primers and probes to amplify and detect and/or quantitate Babesia nucleic acid and/or molecule targets are provided by the embodiments in the present disclosure.

For detection and/or quantitation of Babesia, primers and probes to amplify and detect/quantitate the Babesia are provided. Babesia nucleic acids other than those exemplified herein can also be used to detect Babesia in a sample. For example, functional variants can be evaluated for specificity and/or sensitivity by those of skill in the art using routine methods. Representative functional variants can include, e.g., one or more deletions, insertions, and/or substitutions in the Babesia nucleic acids disclosed herein.

More specifically, embodiments of the oligonucleotides each include a nucleic acid with a sequence selected from SEQ ID NOs:1-7, a substantially identical variant thereof in which the variant has at least, e.g., 80%, 90%, or 95% sequence identity to one of SEQ ID NOs:1-7, or a complement of SEQ ID NOs:1-7 and the variant.

TABLE 1

Oligonucleotides in Babesia Test

| Oligo Name | Oligo Type | SEQ ID NO: | Sequence | Modifications |
|---|---|---|---|---|
| 395_21F_TBB | Forward Primer | 1 | ACCTGCTAAATTAGGATCTGGGJ | J: t-Butyl Benzyl-dA |
| 395_56P_HQ10 | Sense Probe | 2 | HCTGTTCCAGTQATCGCTTCTTAGAGGGACTTTGCP | H: HEX-Thr P: Phosphate Q: BHQ-2 |
| 395_123R_TBB | Reverse Primer | 3 | TGTTATTGCCTTACACTTCCTTGK | K: t-Butyl Benzyl-dC |
| DDVF | Forward Primer | 4 | GATGTCCTGGGCTGCJ | J: t-Butyl Benzyl-dA |
| DDVP_HQ8 | Anti-Sense Probe | 5 | HAACTCGATQGAATGCATCAGTGTAGCGCGP | H: HEX-Thr P: Phosphate Q: BHQ-2 |
| DDVR | Reverse Primer | 6 | CCCCGTCACGATGCATACTAAJ | J: t-Butyl Benzyl-dA |
| DDVR2 | Reverse Primer | 7 | CCCCATCACGATGCATACTAAJ | J: t-Butyl Benzyl-dA |

In one embodiment, the above described sets of Babesia primers and probes are used in order to provide for detection of Babesia in a biological sample suspected of containing Babesia (Table 1). The sets of primers and probes may comprise or consist of the primers and probes specific for the Babesia nucleic acid sequences, comprising or consisting of the nucleic acid sequences of SEQ ID NOs:1-7. In another embodiment, the primers and probes for the Babesia target comprise or consist of a functionally active variant of any of the primers and probes of SEQ ID NOs: 1-7.

A functionally active variant of any of the primers and/or probes of SEQ ID NOs:1-7 may be identified by using the primers and/or probes in the disclosed methods. A functionally active variant of a primer and/or probe of any of the SEQ ID NOs:1-7 pertains to a primer and/or probe which provide a similar or higher specificity and sensitivity in the described method or kit as compared to the respective sequence of SEQ ID NOs:1-7.

The variant may, e.g., vary from the sequence of SEQ ID NOs:1-7 by one or more nucleotide additions, deletions or substitutions such as one or more nucleotide additions, deletions or substitutions at the 5' end and/or the 3' end of the respective sequence of SEQ ID NOs:1-7. As detailed above, a primer and/or probe may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the Babesia target, e.g., nucleic acids encoding alternative portions of Babesia can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of Babesia. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a Babesia (target) nucleic acid. A "probe" can be referred to as a "detection probe" meaning that it detects the target nucleic acid.

In some embodiments, the described Babesia probes can be labeled with at least one fluorescent label. In one embodiment, the Babesia probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NO:3.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one of Babesia primers and probes nucleic acid molecules (e.g., SEQ ID NOs:1, 2, 3, 4, and 5). Constructs can be used, for example, as control template nucleic acid molecules. Vectors suitable for use are commercially available and/or produced by recombinant nucleic acid technology methods routine in the art. Babesia nucleic acid molecules can be obtained, for example, by chemical synthesis, direct cloning from Babesia, or by nucleic acid amplification.

Constructs suitable for use in the methods typically include, in addition to the Babesia nucleic acid molecules (e.g., a nucleic acid molecule that contains one or more sequences of SEQ ID NOs:1-5), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing Babesia nucleic acid molecules can be propagated in a host cell. As used herein, the term host cell is meant to include prokaryotes and eukaryotes such as yeast, plant and animal cells. Prokaryotic hosts may include E. coli, Salmonella typhimurium, Serratia marcescens, and Bacillus subtilis. Eukaryotic hosts include yeasts such as S. cerevisiae, S. pombe, Pichia pastoris, mammalian cells such as COS cells or Chinese hamster ovary (CHO) cells, insect cells, and plant cells such as Arabidopsis thaliana and Nicotiana tabacum. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described Babesia nucleic acid sequences (e.g., SEQ ID NOs:1, 2, 4, and 5). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

The genome of a retrovirus or RNA virus, is comprised of a ribonucleic acid, i.e., RNA. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction.

PCR assays can employ *Babesia* nucleic acid such as RNA or DNA (cDNA). The template nucleic acid need not be purified; it may be a minor fraction of a complex mixture, such as *Babesia* nucleic acid contained in human cells. *Babesia* nucleic acid molecules may be extracted from a biological sample by routine techniques such as those described in *Diagnostic Molecular Microbiology: Principles and Applications* (Persing et al. (eds), 1993, American Society for Microbiology, Washington, D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs:1, 2, 4, and 5) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target *Babesia* nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety or dye (e.g., HEX or FAM) and a corresponding quencher (e.g., BlackHole Quencher™ (BHQ) (such as BHQ-2)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quencher™ (BHQ) (such as BHQ2), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the *Babesia* target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, *Lucifer* Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of *Babesia* Amplified Product (Amplicon)

The present disclosure provides methods for detecting the presence or absence of *Babesia* in a biological or non-biological sample. Methods provided avoid problems of sample contamination, false negatives, and false positives. The methods include performing at least one cycling step that includes amplifying a portion of *Babesia* target nucleic acid molecules from a sample using one or more pairs of *Babesia* primers, and a FRET detecting step. Multiple cycling steps are performed, preferably in a thermocycler. Methods can be performed using the *Babesia* primers and probes to detect the presence of *Babesia*, and the detection of *Babesia* indicates the presence of *Babesia* in the sample.

As described herein, amplification products can be detected using labeled hybridization probes that take advantage of FRET technology. One FRET format utilizes TaqMan® technology to detect the presence or absence of an amplification product, and hence, the presence or absence of *Babesia*. TaqMan® technology utilizes one single-stranded hybridization probe labeled with, e.g., one fluorescent moiety or dye (e.g., HEX or FAM) and one quencher (e.g., BHQ-2), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of *Babesia* in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of *Babesia* genomes). If amplification of *Babesia* target nucleic acid occurs and an amplification product is produced, the step of hybridizing results in a detectable signal based upon FRET between the members of the pair of probes.

Generally, the presence of FRET indicates the presence of *Babesia* in the sample, and the absence of FRET indicates the absence of *Babesia* in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to whole blood, respiratory specimens, urine, fecal specimens, blood specimens, plasma, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release *Babesia* nucleic acid or in some cases, the biological sample can be contacted directly with the PCR reaction components and the appropriate oligonucleotides. In some instances, the biological sample is whole blood. When whole blood is typically collected, it is often collected in vessels containing anticoagulants, such as heparin, citrate, or EDTA, which enables the whole blood to be stored at suitable temperatures. However, under such conditions, the nucleic acids within the whole blood undergo considerable amount of degradation. Therefore, it may be advantageous to collect the blood in a reagent that will lyse, denature, and stabilize whole blood components, including nucleic acids, such as a nucleic acid-stabilizing solution. In such cases, the nucleic acids can be better preserved and stabilized for subsequent isolation and analysis, such as by nucleic acid test, such as PCR. Such nucleic acid-stabilizing solution are well known in the art, including, but not limited to, cobas PCR media, which contains 4.2 M guanadinium salt (GuHCl) and 50 mM Tris, at a pH of 7.5.

The sample can be collected by any method or device designed to adequately hold and store the sample prior to analysis. Such methods and devices are well known in the art. In the case that the sample is a biological sample, such as whole blood, the method or device may include a blood collection vessel. Such a blood collection vessel is well known in the art, and may include, for example, a blood collection tube. In many cases, it may be advantageous to use a blood collection tube wherein the blood collection vessel is under pressure in the space intended for sample uptake, such as a blood vessel with an evacuated chamber, such as a vacutainer blood collection tube. Such blood collection tubes with an evacuated chamber, such as a vacutainer blood collection tube are well known in the art. It may further be advantageous to collect the blood in a blood collection vessel, with or without an evacuated chamber, that contains within it, a solution that will lyse, denature, and stabilize whole blood components, including nucleic acids, such as a nucleic acid-stabilizing solution, such that the whole blood being drawn immediately contacts the nucleic acid-stabilizing solution in the blood collection vessel.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the *Babesia* probes from the *Babesia* amplification products can confirm the presence or absence of *Babesia* in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3 SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect *Babesia*. An article of manufacture can include primers and probes used to detect the *Babesia* gene target, together with suitable packaging materials. Representative primers and probes for detection of *Babesia* are capable of hybridizing to *Babesia* target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to *Babesia* target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the *Babesia* probes. Examples of suitable FRET donor fluorescent moieties and corresponding acceptor fluorescent moieties are provided above.

Articles of manufacture can also contain a package insert or package label having instructions thereon for using the *Babesia* primers and probes to detect *Babesia* in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure also provide for a set of primers and one or more detectable probes for the detection of *Babesia* in a sample.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

The test was a fully automated sample preparation (nucleic acid extraction and purification) followed by PCR amplification and detection. The system used was the Cobas® 6800/8800 System, which consisted of a sample supply module, the transfer module, the processing module, and the analytic module. Automated data manage was performed by the Cobas® 6800/8800 System.

Selective amplification of target nucleic acid was achieved by the use of specific forward and reverse primers which were selected from highly conserved regions of the target nucleic acid. A thermostable DNA polymerase enzyme was used for both reverse-transcription and amplification. The master mix included deoxyuridine triphosphate (dUTP), instead of deoxythimidine triphosphate (dTTP), which is incorporated into the newly synthesized DNA (amplified product or amplicon). Any contaminating amplicons from previous PCR runs were destroyed by the AmpErase enzyme (uracil-N-glycosylase), which was included in the PCR mix, when heated in the first thermal cycling step. Newly formed amplicons were not destroyed, however, since the AmpErase enzyme was inactivated once exposed to temperatures above 55° C.

The Cobas® *Babesia* master mix contained detection probes which were specific for *Babesia* and control nucleic acids. The specific *Babesia* and control detection probes were each labeled with one of two unique fluorescent dyes which act as a reporter. Each probe also had a second dye which acted as a quencher. The reporter dye is measured at a defined wavelength, thus permitting detection and discrimination of the amplified *Babesia* target and the control. The fluorescent signal of the intact probes was suppressed by the quencher dye. During the PCR amplification step, hybridization of the probes to the specific single-stranded DNA template resulted in cleavage by the 5' to 3' nuclease activity of the DNA polymerase resulting in separation of the reporter and quencher dyes, and the generation of fluorescent signal. With each PCR cycle, increasing amounts of cleaved probes were generated and the cumulative signal of the reporter dye was concomitantly increased. Because the two specific reporter dyes are measured at defined wavelengths, simultaneous detection and discrimination of the amplified *Babesia* target and the control was possible.

The primers and probes for the *Babesia* test were designed by seeding primers and probes along the genome in the most conserved regions based on the alignment. The primers and probes were then combined into assays and the assays were scored based on the inclusivity and exclusivity in-silico assessment. In addition to genomic conservation, genomic coverage (which is highly dependent on what sequences are available publicly) was also included in the scoring of the assays. The targeted region of the *Babesia* genome was the 18S gene for the *Babesia* species *B. microti, B. divergens, B. duncani*, and *B. venatorum*. One set of oligonucleotides (SEQ ID NOs:1-3) was designed to detect *B. microti*, which is often referred herein as "395," and another set of oligonucleotides (SEQ ID NOs:4-7) was designed to detect *B. divergens, B. duncani*, and *B. venatorum*. The set of oligonucleotides designed to detect *B. divergens, B. duncani*, and *B. venatorum* included two different sets of oligonucleotides, as follows: (1) the first set included oligonucleotides SEQ ID NOs:4-6 (often referred, herein, as "DDVR"); and (2) the second set included oligonucleotides SEQ ID NOs:4-7 (often referred, herein, as "DDVR2").

Example 1: Amplification and Detection of *B. microti* by Real-Time PCR

Figure 2:
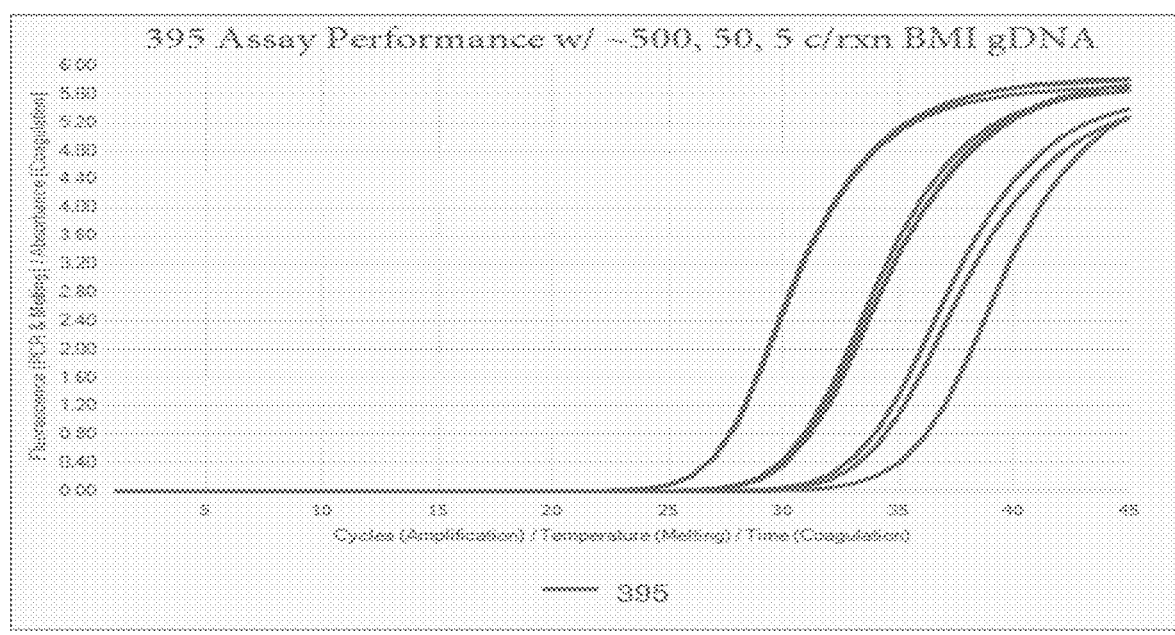
FIG. 2 shows real time PCR growth curves of the *B. microti* nucleic acid test ("395") on *B. microti* genomic DNA (ATCC 30221D) dilutions (using primers having a nucleic acid sequence of SEQ ID NOs:1 and 3 and a probe having a nucleic acid sequence of SEQ ID NO:2).

The *B. microti* nucleic acid test for the *Babesia* 18S rRNA gene was tested using an oligonucleotide set designed to amplify and detect *B. microti* (forward primer SEQ ID NO:1, reverse primer SEQ ID NO:3, and probe SEQ ID NO:2), and using either pEF113 (*B. microti* strain Gray in pUC19) (FIG. 1) or *B. microti* genomic DNA (FIG. 2). Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 µM for primers and 0.1 µM for probes. The Cobas® 6800/8800 PCR Profile employed is depicted in Table 2, below:

TABLE 2 cobas ® 6800/8800 PCR Profile

| Step | Cycles | Target (° C.) | Hold time (hh:mm:ss) | Ramp |
|---|---|---|---|---|
| Pre-PCR | 1 | 50 | 00:02:00 | 4.4 |
|  |  | 94 | 00:00:05 | 4.4 |
|  |  | 55 | 00:02:00 | 2.2 |
|  |  | 60 | 00:06:00 | 4.4 |
|  |  | 65 | 00:04:00 | 4.4 |
| 1. Meas | 5 | 95 | 00:00:05 | 4.4 |
|  |  | 55 | 00:00:30 | 2.2 |
| 2. Meas | 45 | 91 | 00:00:05 | 4.4 |
|  |  | 58 | 00:00:25 | 2.2 |
| Post | 1 | 40 | 00:02:00 | 2.2 |

These studies show that under these conditions, the oligonucleotides (SEQ ID NOs:1-3) were able to amplify and detect *B. microti* (see, FIGS. 1 and 2).

End point dilution series analysis was also performed to assess the lower limit of detection in this system. The *B. microti* pUC19 plasmid (pEF113) was quantified using ddPCR, diluted, and tested. The results of the end-point dilution analysis are shown below in Table 3.

TABLE 3

|  | 395 |
|---|---|
| 12.5 c/xn | 8/8 |
| 6.25 c/rxn | 8/8 |
| 3.13 c/rxn | 7/8 |
| 1.56 c/rxn | 6/8 |
| 0.78 c/rxn | 2/8 |
| 0.39 c/rxn | 0/8 |
| 0.20 c/rxn | 0/8 |
| 0.1 c/rxn | 0/8 |
| 0.05 c/rxn | 0/8 |
| 0.025 c/rxn | 0/8 |

The limit of detection was determined to be 3.32 copies of plasmid DNA per PCR at 95% confidence.

Thus, these results demonstrate that the primers and probes (SEQ ID NOs:1-3) amplify and detect the presence of *B. microti* efficiently and specifically in a real-time PCR assay.

Figure 3:
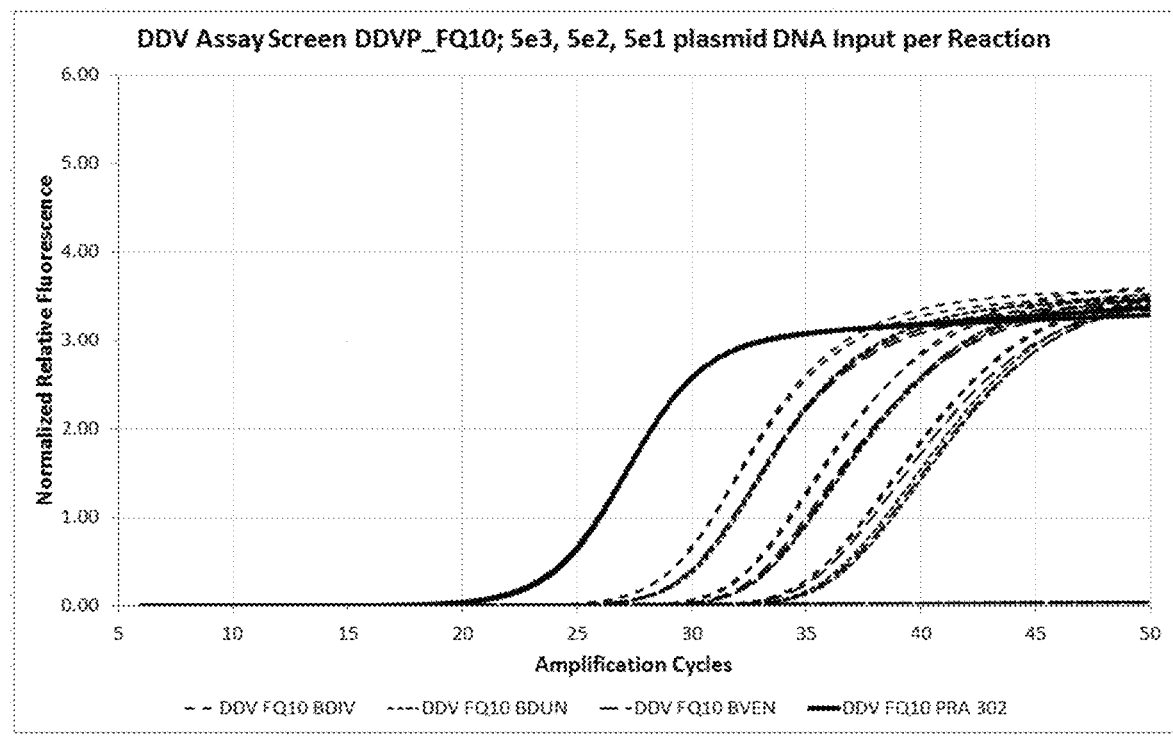
FIG. 3 shows PCR growth curves of the nucleic acid test ("DDV") for *B. divergens, B. duncani*, and *B. venatorum* on plasmids pEF114 (*B. divergens*), pEF115 (*B. duncani*), and pEF116 (*B. venatorum*) and total nucleic acids from *B. duncani* (ATCC PRA 302) (using primers having nucleic acid sequence of SEQ ID NOs:4 and 6 and a probe having nucleic acid sequence of SEQ ID NO:5).

Example 2: Amplification and Detection of *B. divergens*, *B. duncani*, and *B. venatorum* by Real-Time PCR The *B. divergens*, *B. duncani*, and *B. venatorum* (referred here often as "DDV") nucleic acid test for *Babesia* 18S rRNA gene was tested using an oligonucleotide set designed to amplify and detect *B. divergens*, *B. duncani*, and *B. venatorum* (forward primer SEQ ID NO:4, reverse primer SEQ ID NO:6, and probe SEQ ID NO:5), and using plasmids pEF114 (*B. divergens*), pEF115 (*B. duncani*), and pEF116 (*B. venatorum*), or total nucleic acid from *B. duncani* (ATCC PRA 302) (FIG. 3). Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 µM for primers and 0.1 µM for probes. The Cobas® 6800/8800 PCR Profile employed is depicted in Table 2, above. These studies show that under these conditions, the oligonucleotides (SEQ ID NOs:4-6) were able to amplify and detect *B. divergens*, *B. duncani*, and *B. venatorum* (see, FIG. 3).

Thus, these results demonstrate that the primers and probes (SEQ ID NOs:4-6) amplify and detect the presence of *B. divergens, B. duncani*, and *B. venatorum* efficiently and specifically in a real-time PCR assay Example 3: Multiplex Amplification and Detection of *B. microti, B. divergens, B. Duncani*, and *B. venatorum* by Real-Time PCR Because the assay for amplification and detection of *B. microti* (SEQ ID NOs:1-3; Example 1; and FIGS. 1-2) and the assay for amplification and detection of *B. divergens, B. duncani*, and *B. venatorum* ("DDV," SEQ ID NOs:4-6; Example 2; and FIG. 3) showed good performance in singleplex, the assays were tested in a multiplex setting, under the same conditions as described for the singleplex tests.

Figure 4:
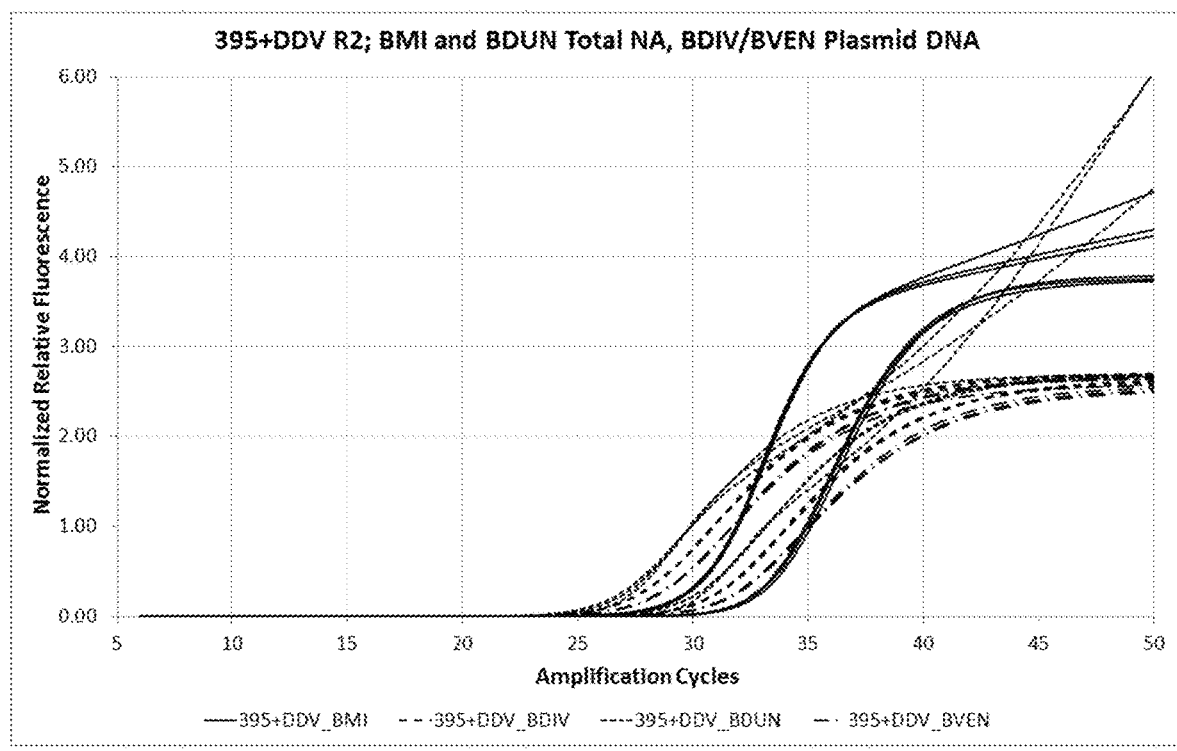
FIG. 4 shows PCR growth curves of the *B. microti* oligonucleotide set ("395," SEQ ID NOs:1-3) and the *B. divergens, B. duncani*, and *B. venatorum* oligonucleotide set ("DDV," SEQ ID NOs:4-6) in a multiplex setting.

FIG. 4 shows, as expected, that the *B. microti* target is amplified and detected strongly by SEQ ID NOs:1-3, in a multiplex setting, and is amplified and detected weakly by the DDV oligonucleotides (i.e., SEQ ID NOs:4-6). Similarly, FIG. 4 also shows that *B. divergens, B. duncani*, and *B. venatorum* are not amplified and detected by SEQ ID NOs:1-3, but are strongly amplified and detected by the DDV oligonucleotides (i.e., SEQ ID NOs:4-6).

Example 4: Optimization of Spacings Between Fluorophore and Quencher of Probe

Figure 5:
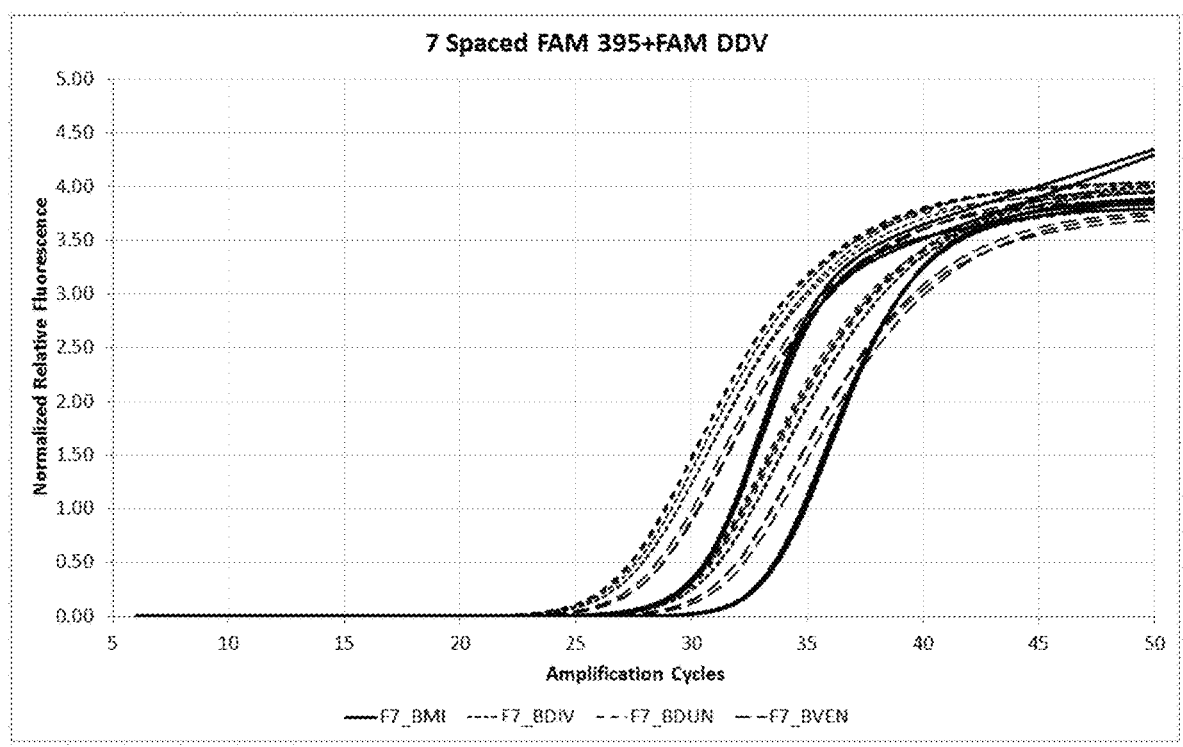
FIG. 5 shows PCR growth curves of the *B. microti* probe (SEQ ID NO:2) at a spacing of 7 bases between the fluorophore and quencher, in order to determine optimal spacing.
Figure 6:
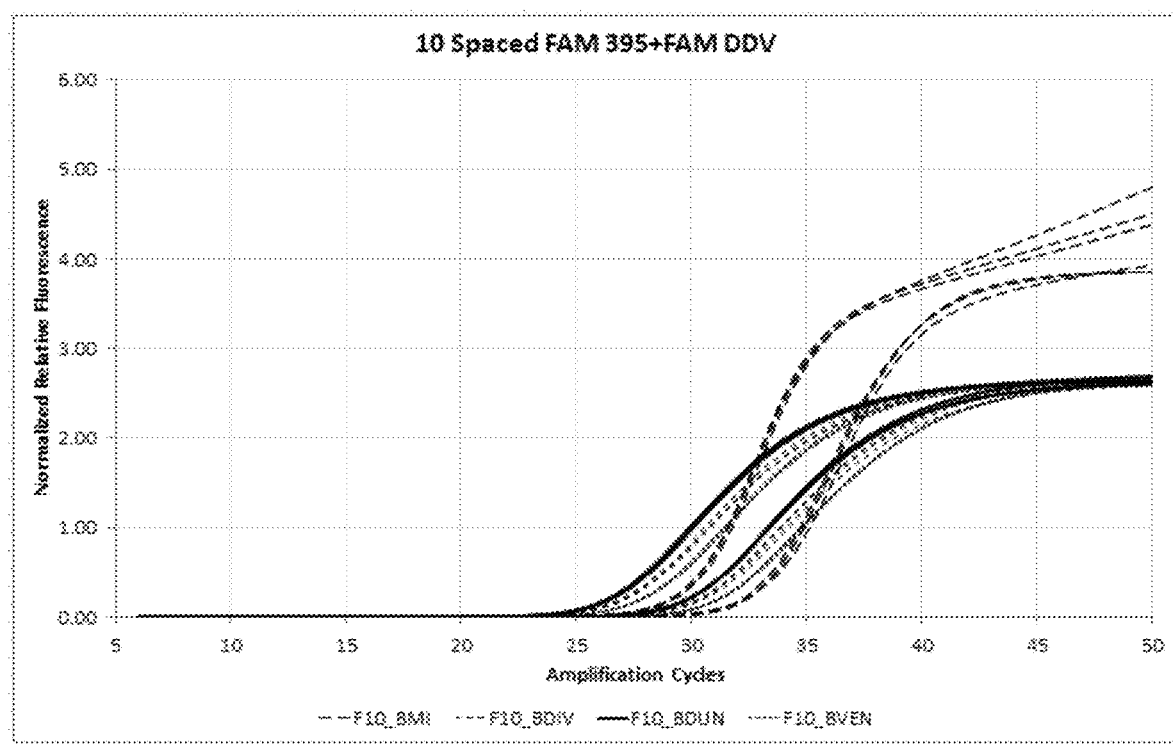
FIG. 6 shows PCR growth curves of the *B. microti* probe (SEQ ID NO:2) at a spacing of 10 bases between the fluorophore and quencher, in order to determine optimal spacing.

The *B. microti* probe (i.e., SEQ ID NO:2) was evaluated with different spacings between the fluorophore and quencher to determine the optimal spacing (see, FIG. 5). The assays were tested under the same conditions as described previously, in Examples 1-3. Although the probe was effective at a spacing of seven and 10 bases in between fluorophore and quencher, the 10-spaced probe exhibited similar endpoint RFI and better inclusivity (see, FIGS. 5 and 6).

Thus, the *Babesia* probes are efficient and specific within a wide range of spacing between the fluorophore and quencher, including between 7-10 bases.

Example 5: Optimization of Probe Dyes

Figure 7:
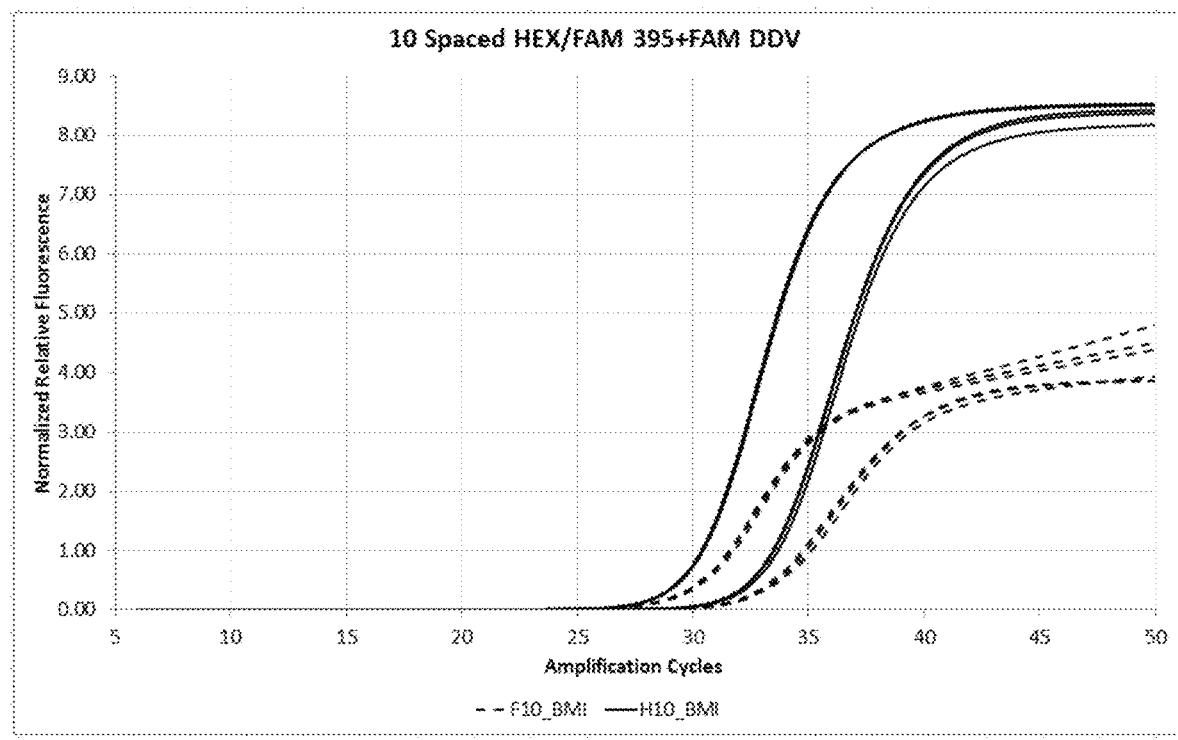
FIG. 7 shows PCR growth curves of the *B. microti* probe (SEQ ID NO:2) evaluated with different dyes (FAM and HEX), in order to determine the optimal dye.

The *B. microti* probe (i.e., SEQ ID NO:2) was evaluated with different fluorescent moieties or fluorescent dyes, FAM and HEX. Assays were tested under the same conditions as described previously, in Examples 1-4. Although the probe was effective with either FAM or HEX fluorescent moieties/dyes, the HEX-labeled probe demonstrated a lower baseline, leading to greatly increased signal (see, FIG. 7).

Thus, the *Babesia* probes are efficient and specific with a number of different types of fluorescent moieties/dyes, including FAM and HEX.

Example 6: Post-PCR Analysis

Figure 8:
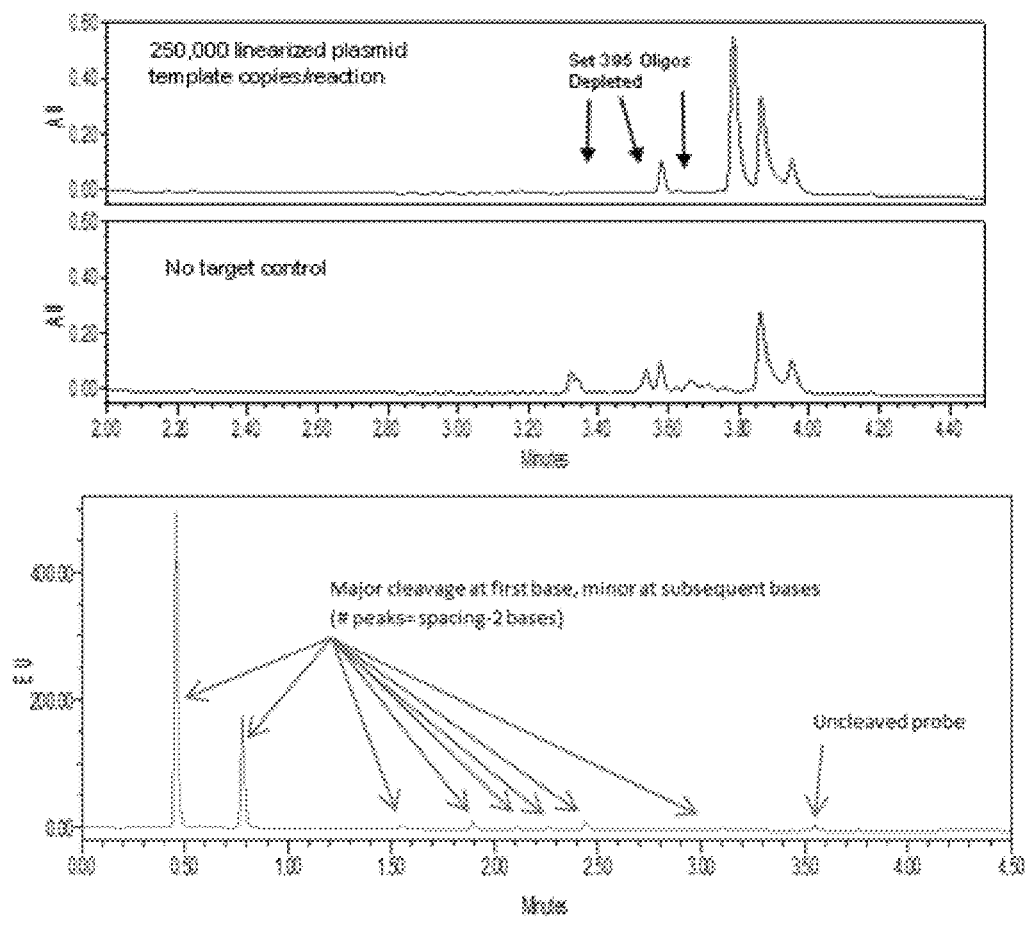
FIG. 8 shows post-PCR analysis of the *B. microti* oligonucleotide set ("395," SEQ ID NOs:1-3), which demonstrates efficient amplification, as evidenced by depletion of oligonucleotides and efficient cleavage of the probe.

A post-PCR analysis was performed with the oligonucleotides detecting *B. microti* (SEQ ID NOs:1-3). This post- PCR analysis was performed in order to ensure efficient amplification as evidenced by depletion of oligonucleotides and efficient cleavage of the probe. As can be seen in FIG. 8, the *B. microti* oligonucleotides (SEQ ID NOs:1-3) demonstrates depletion of oligonucleotides and probe cleavage.

Thus, the *Babesia* oligonucleotides ensure efficient amplification, as evidenced by depletion of oligonucleotides and efficient cleavage of the probe.

Example 7: Multiplex Amplification and Detection of *B. microti*, *B. divergens*, *B. Duncani*, and *B. venatorum* by Real-Time PCR in Whole Blood The oligonucleotides for amplification and detection of *B. microti*, *B. divergens*, *B. duncani*, and *B. venatorum* were tested in whole blood. Briefly, secondary standard was made by lysing *Babesia* culture in cobas PCM media (CPM). Cobas PCR media is a pre-analytic reagent that lyses, denatures, and stabilizes whole blood components, including nucleic acids. Cobas PCR media contains guanidinium salt (here, GuHCl at 4.2 M) and Tris (here, 50 mM), at a pH of 7.5. Four separate standards for four different *Babesia* species (*B. microti*, *B. divergens*, *B. duncani*, and *B. venatorum*) were generated in this manner. The secondary standard was diluted to intermediate levels in cobas PCR media, then spiked into a whole blood:cobas PCR media mixture. The whole blood:cobas PCR media mixture is 1 part whole blood, and 7 parts cobas PCR media. The final concentrations of each standard were as shown below in Table 4.

TABLE 4

Standard Concentrations

| Babesia Strain | Concentration (iRBC/ml) |
|---|---|
| B. microti | 0.375 |
| B. divergens | 5.700 |
| B. duncani | 4.088 |
| B. venatorum | 500 |

Figure 9:
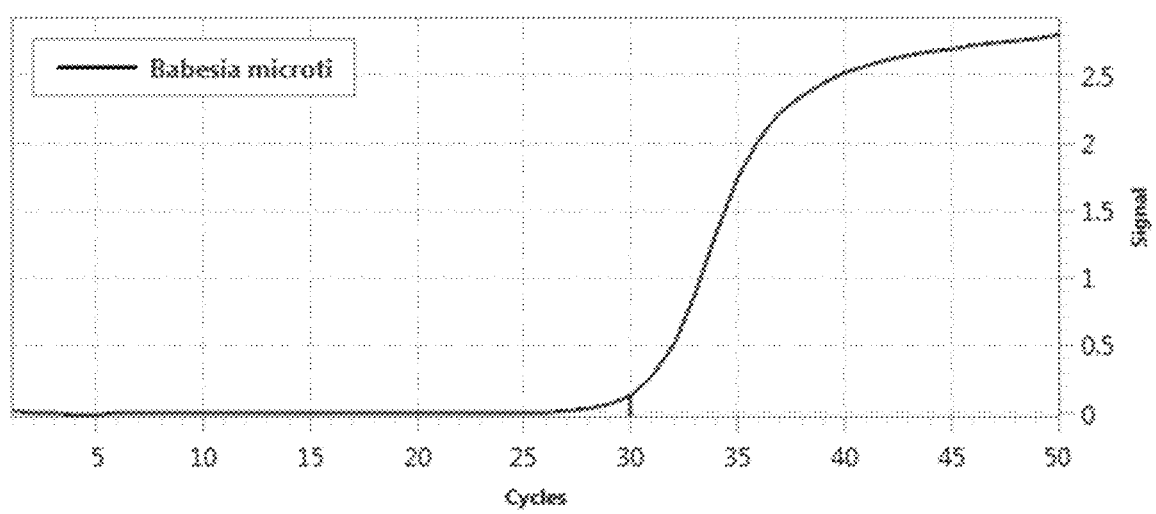
FIG. 9 shows a PCR growth curve for *B. microti* using the *B. microti* oligonucleotide set ("395," SEQ ID NOs:1-3) and the *B. divergens, B. duncani*, and *B. venatorum* oligonucleotide set ("DDV," SEQ ID NOs:4-6) in a multiplex setting in whole blood (treated with cobas PCR media).
Figure 10:
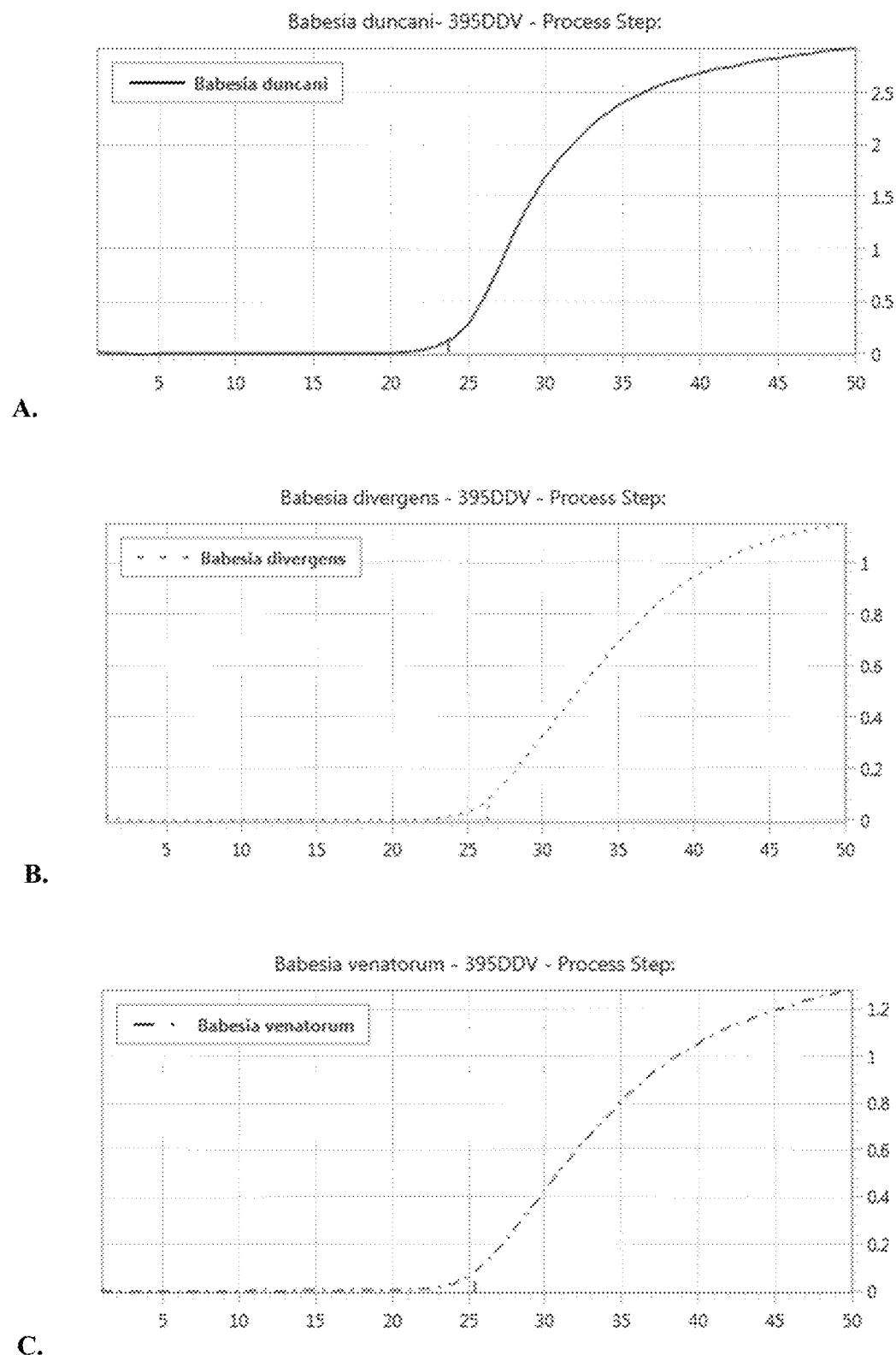
FIG. 10 shows PCR growth curves for *B. duncani* (FIG. 10A), *B. divergens* (FIG. 10B), and *B. venatorum* (FIG. 10C) using the *B. microti* oligonucleotide set ("395," SEQ ID NOs:1-3) and the *B. divergens, B. duncani*, and *B. venatorum* oligonucleotide set ("DDV," SEQ ID NOs:4-6) in a multiplex setting in whole blood (treated with cobas PCR media).
Figure 11:
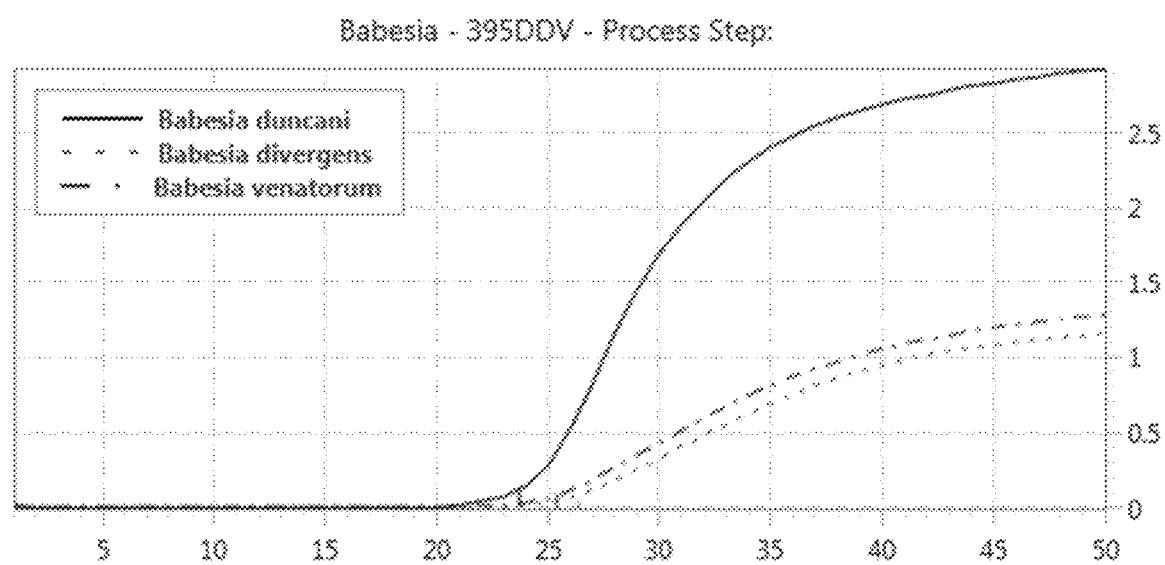
FIG. 11 shows the overlay of FIGS. 10A, 10B, and 10C in a single figure, showing PCR growth curves for *B. duncani, B. divergens*, and *B. venatorum*, using the *B. microti* oligonucleotide set ("395," SEQ ID NOs:1-3) and the *B. divergens, B. duncani*, and *B. venatorum* oligonucleotide set ("DDV," SEQ ID NOs:4-6) in a multiplex setting in whole blood (treated with cobas PCR media).

The standard-spiked whole blood was subjected to oligonucleotides for amplification and detection of *B. microti*, *B. divergens*, *B. duncani*, and *B. venatorum* (SEQ ID NOs:1-3 and 4-6), under conditions as described previously (Examples 1-6). Results are shown in FIG. 9-11. FIG. 9 reveals that the oligonucleotide set of SEQ ID NOs:1-3 to detect *B. microti* in combination with the oligonucleotide set of SEQ ID NOs:4-6 to detect *B. divergens*, *B. duncani*, and *B. venatorum* (in a multiplex setting) were able to specifically and efficiently amplify and detect *B. microti* in whole blood. FIGS. 10-11 reveal that the oligonucleotide set of SEQ ID NOs:1-3 to detect *B. microti* in combination with the oligonucleotide set of SEQ ID NOs:4-6 to detect *B. divergens*, *B. duncani*, and *B. venatorum* (in a multiplex setting) were able to specifically and efficiently amplify and detect *B. divergens* (FIGS. 10A and 11), *B. duncani* (FIGS. 10B and 11), and *B. venatorum* (FIGS. 10C and 11) in whole blood. Thus, these results demonstrate that the oligonucleotide set of SEQ ID NOs:1-6 specifically and efficiently amplify and detect *B. microti*, *B. divergens*, *B. duncani*, and *B. venatorum* in whole blood. These results also demonstrate that cobas PCR media that lyses, denatures, and stabilizes whole blood components, including nucleic acids Example 8: Multiplex Amplification and Detection of *B. microti*, *B. divergens*, *B. Duncani*, and *B. venatorum* by Real-Time PCR in Whole Blood with Pair of Reverse Primers for *B. divergens*, *B. duncani*, and *B. venatorum*

Further studies were conducted to demonstrate multiplex amplification and detection of *B. microti*, *B. divergens*, *B. duncani*, and *B. venatorum* by real-time PCR in whole blood, as above in Example 7, but with use of a pair of reverse primers for amplification and detection of *B. divergens*, *B. duncani*, and *B. venatorum*. That is, a new oligonucleotide set for the amplification and detection of *B. divergens*, *B. duncani*, and *B. venatorum* was tested. In particular, a new reverse primer, SEQ ID NO:7 was used in concert with reverse primer SEQ ID NO:6. The two different reverse primers (SEQ ID NOs:6 and 7) were then used in combination with forward primer SEQ ID NO:4 and probe SEQ ID NO:5, designed to amplify and detect *B. divergens*, *B. duncani*, and *B. venatorum*. The oligonucleotide set of SEQ ID NOs:4-7 designed to detect *B. divergens*, *B. duncani*, and *B. venatorum* was then combined with the oligonucleotide set of SEQ ID NOs:1-3 designed to detect *B. microti* to investigate of the combined oligonucleotide set of SEQ ID NOs:1-7 could amplify and detect *B. microti*, *B. divergens*, *B. duncani*, and *B. venatorum* in whole blood. The conditions were identical to as described for the previous whole blood studies described previously. The final concentrations of each standard were as shown below in Table 5.

TABLE 5

Standard Concentrations

| Babesia Strain | Concentration (iRBC/ml) |
|---|---|
| B. microti | 0.375 |
| B. divergens | 5.700 |
| B. duncani | 4.088 |
| B. venatorum | 12.5 |

Figure 12:
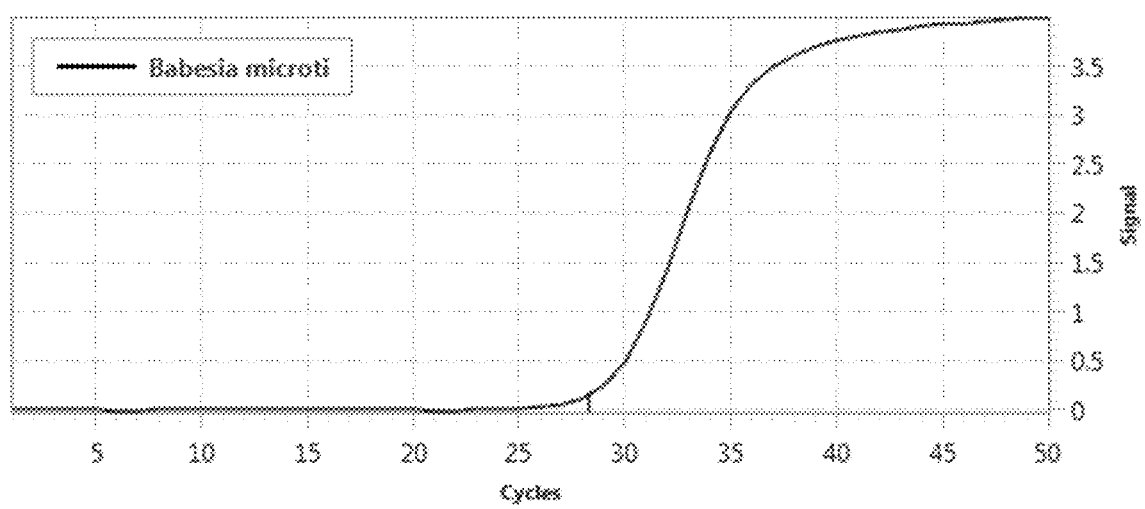
FIG. 12 shows a PCR growth curve for *B. microti* using the *B. microti* oligonucleotide set ("395," SEQ ID NOs:1-3) and the *B. divergens, B. duncani*, and *B. venatorum* oligonucleotide set ("DDVR2," SEQ ID NOs:4-7, with a mix of equal amounts of reverse primers SEQ ID NOs:6 and 7) in a multiplex setting in whole blood (treated with cobas PCR media).
Figure 13:
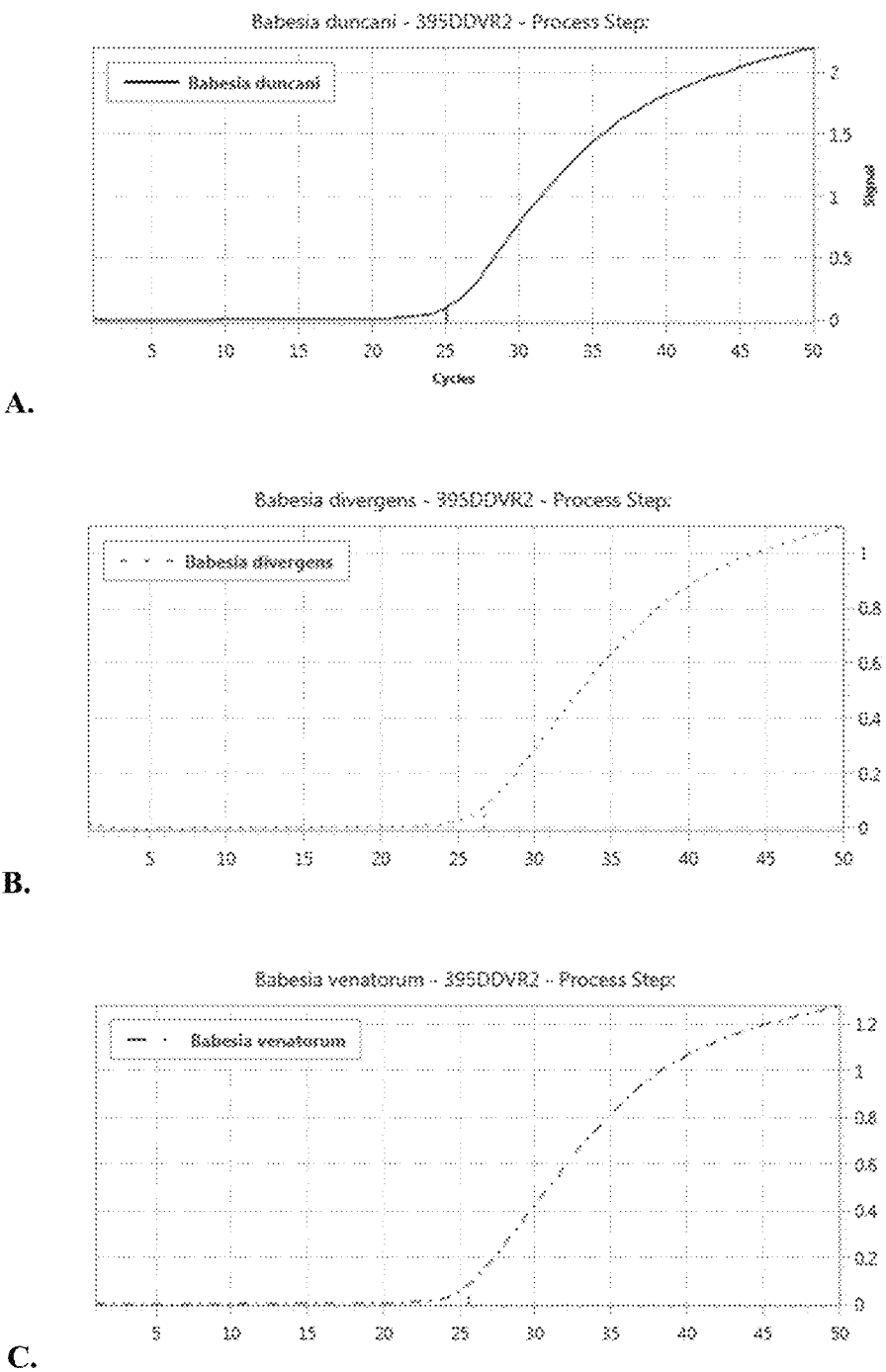
FIG. 13 shows PCR growth curves for *B. duncani* (FIG. 13A), *B. divergens* (FIG. 13B), and *B. venatorum* (FIG. 13C) using the *B. microti* oligonucleotide set ("395," SEQ ID NOs:1-3) and the *B. divergens, B. duncani*, and *B. venatorum* oligonucleotide set ("DDVR2," SEQ ID NOs:4-7, with a mix of equal amounts of reverse primers SEQ ID NOs:6 and 7) in a multiplex setting in whole blood (treated with cobas PCR media).
Figure 14:
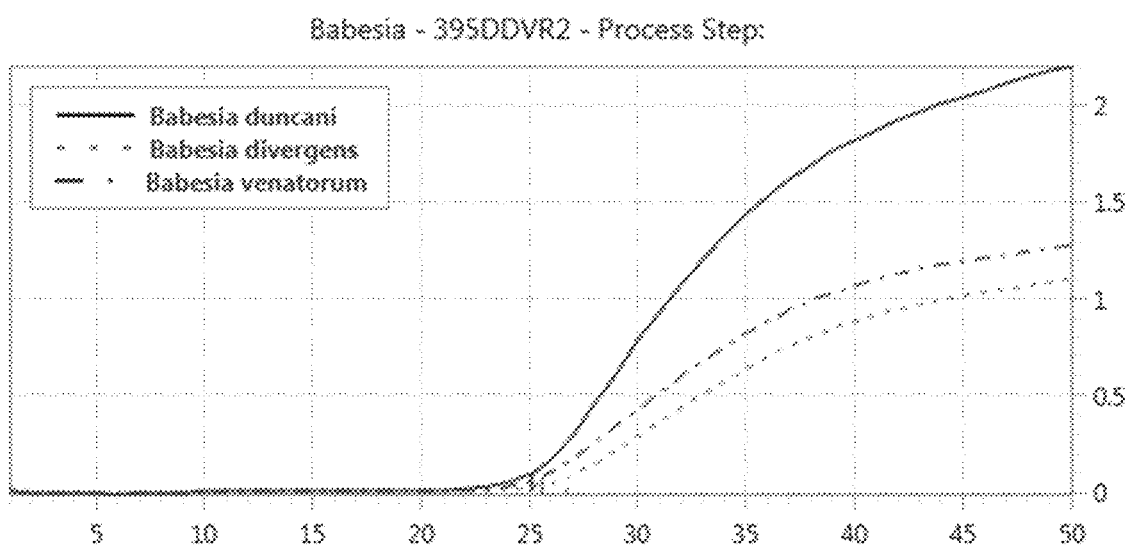
FIG. 14 shows the overlay of FIGS. 13A, 13B, and 13C in a single figure, showing PCR growth curves for *B. duncani, B. divergens*, and *B. venatorum*, using the *B. microti* oligonucleotide set ("395," SEQ ID NOs:1-3) and the *B. divergens, B. duncani*, and *B. venatorum* oligonucleotide set ("DDV," SEQ ID NOs:4-6) in a multiplex setting in whole blood (treated with cobas PCR media)

Results are shown in FIG. 12-14. FIG. 12 reveals that the oligonucleotide set of SEQ ID NOs:1-3 to detect *B. microti* in combination with the oligonucleotide set of SEQ ID NOs:4-7 to detect *B. divergens*, *B. duncani*, and *B. venatorum* (in a multiplex setting) were able to specifically and efficiently amplify and detect *B. microti* in whole blood. FIGS. 13-14 reveal that the oligonucleotide set of SEQ ID NOs:1-3 to detect *B. microti* in combination with the oligonucleotide set of SEQ ID NOs:4-7 to detect *B. divergens*, *B. duncani*, and *B. venatorum* (in a multiplex setting) were able to specifically and efficiently amplify and detect *B. divergens* (FIGS. 13A and 14), *B. duncani* (FIGS. 13B and 14), and *B. venatorum* (FIGS. 13C and 14) in whole blood.

Figure 15:
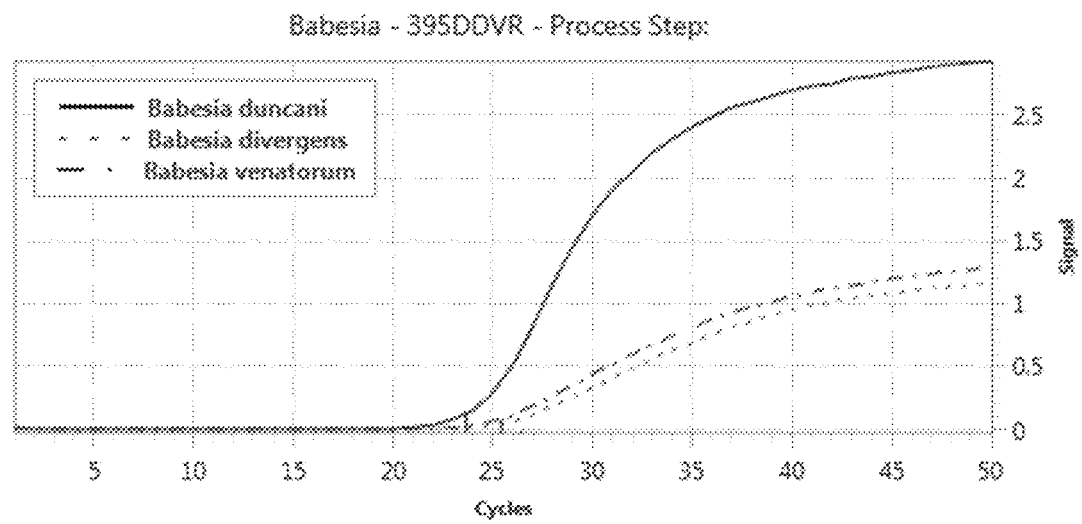
FIG. 15 shows PCR growth curves for *B. duncani, B. divergens*, and *B. venatorum* using a first oligonucleotide set (SEQ ID NOs:1-6) (FIG. 15A) and a second oligonucleotide set (SEQ IQ NOs:1-7, with a mix in equal amounts of reverse primers SEQ ID NOs:6 and 7) (FIG. 15B), in a multiplex setting in whole blood (treated with cobas PCR media).
Figure 15:
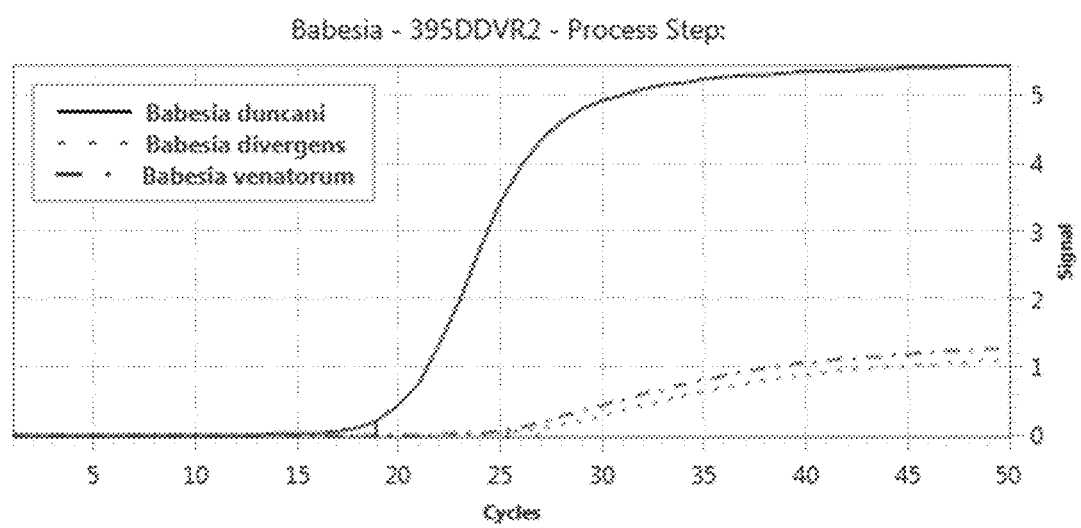
Figure 16:
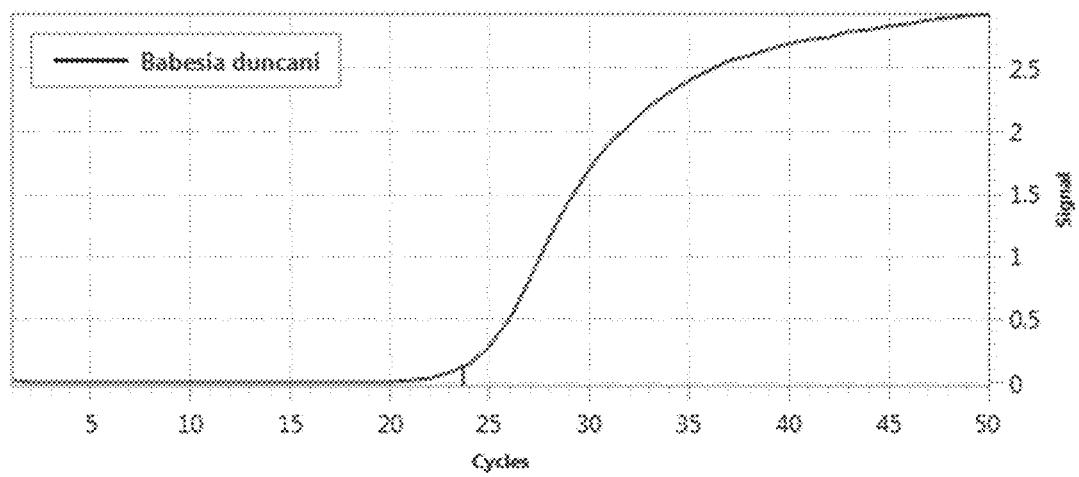
FIG. 16 shows PCR growth curves for *B. duncani*, using a first oligonucleotide set (SEQ ID NOs:1-6) (FIG. 16A) and a second oligonucleotide set (SEQ IQ NOs:1-7, with a mix in equal amounts of reverse primers SEQ ID NOs:6 and 7) (FIG. 16B), in a multiplex setting in whole blood (treated with cobas PCR media).
Figure 16:
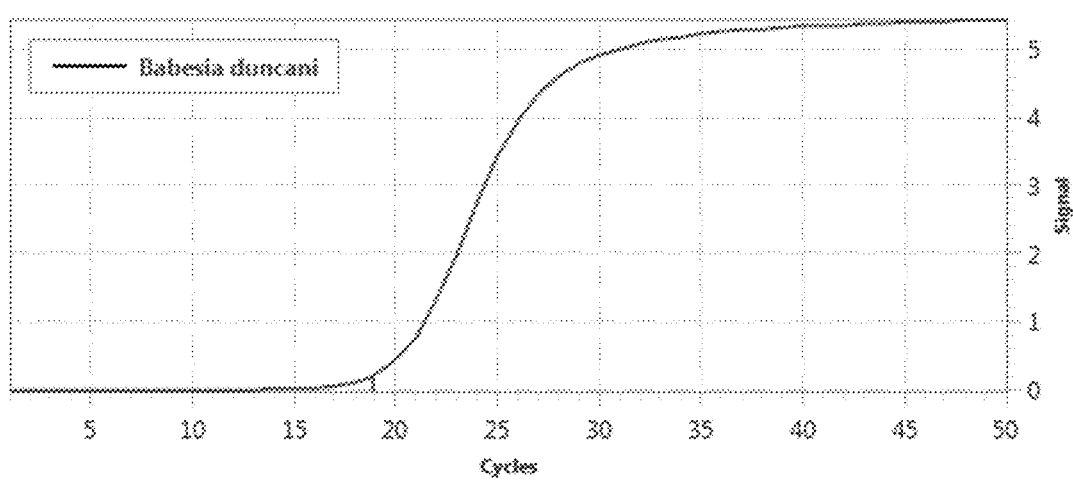
Figure 17:
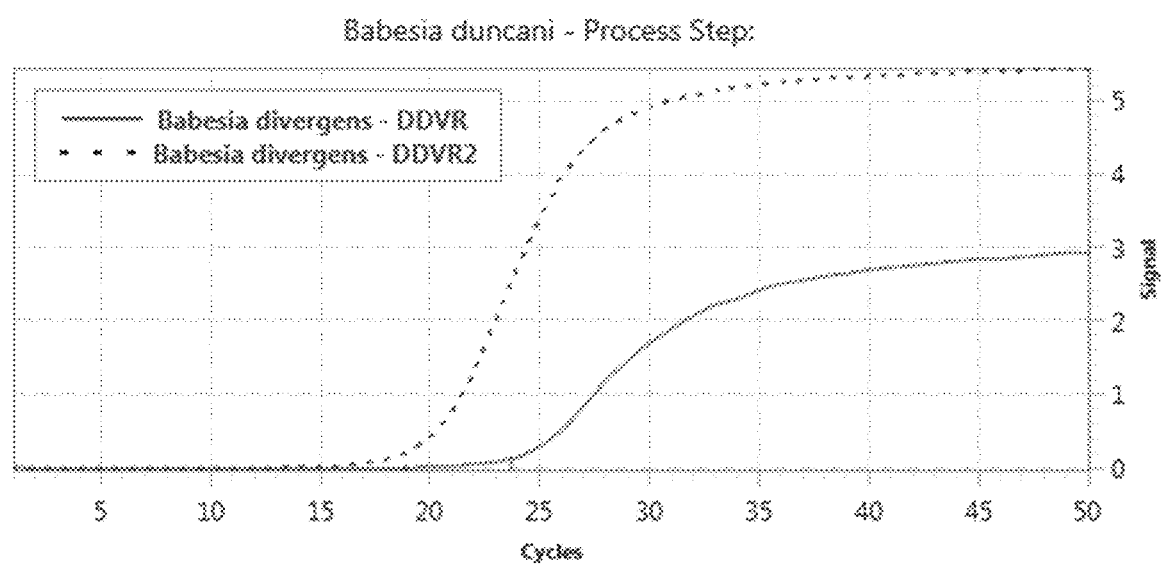
FIG. 17 shows the overlay of FIGS. 16A and 16B in a single figure, showing PCR growth curves for *B. duncani*, using a first oligonucleotide set (SEQ ID NOs:1-6) (labeled "DDVR") and a second oligonucleotide set (SEQ IQ NOs: 1-7, with a mix in equal amounts of reverse primers SEQ ID NOs:6 and 7) (labeled "DDVR2"), in a multiplex setting in whole blood (treated with cobas PCR media).

These experiments were then reproduced to compare the oligonucleotide set SEQ ID NOs:1-6 versus the oligonucleotide set SEQ ID NOs:1-7 in their abilities to detect and amplify *B. microti* (data not shown), *B. divergens*, *B. duncani*, and *B. venatorum* in whole blood. These results are shown in FIG. 15. The oligonucleotide set of SEQ ID NOs:1-7 employed two reverse primers, SEQ ID NOs:6 and 7, in equal amounts. FIG. 15 shows the curves for *B. divergens*, *B. duncani*, and *B. venatorum* using the oligonucleotide set of SEQ ID NOs:1-6 (FIG. 15A) versus the oligonucleotide set of SEQ ID NOs:1-7 (FIG. 15B). In particular, the PCR curves for *B. duncani* were analyzed (FIGS. 16-17). These data reveal that the oligonucleotide set SEQ ID NO:1-7 (FIG. 16B) exhibited improved amplification of *B. duncani* as compared to the oligonucleotide set of SEQ ID NO:6 (FIG. 16A). That is, while the oligonucleotide set of SEQ ID NO:1-6 (which included a single reverse primer, SEQ ID NO:6, to amplify *B. divergens, B. duncani,* and *B. venatorum*) is able to successfully amplify and detect *B. divergens, B. duncani,* and *B. venatorum*, the oligonucleotide set of SEQ ID NOs:1-7 (which included two reverse primers, SEQ ID NO:6 and 7 in equal amounts, to amplify *B. divergens, B. duncani,* and *B. venatorum*), the pair of reverse primers (SEQ ID NOs:6 and 7) exhibited improved amplification of *B. duncani* (FIG. 17).

Thus, these results demonstrate that the oligonucleotide set of SEQ ID NOs:1-6 specifically and efficiently amplify and detect *B. microti, B. divergens, B. duncani,* and *B. venatorum* in whole blood. These results also demonstrate that cobas PCR media that lyses, denatures, and stabilizes whole blood components, including nucleic acids.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

---

What is claimed:

1. A method of detecting the *Babesia* species of (i) *B. microti*; and/or (ii) *B. divergens, B. duncani*, and/or *B. venatorum* in a sample, the method comprising:
   (a) performing an amplification step comprising contacting the sample with one or more set of primers to produce an amplification product, if a target nucleic acid of (i) *B. microti*, and/or (ii) *B. divergens, B. duncani*, and/or *B. venatorum* is present in the sample;
   (b) performing a hybridization step comprising contacting the amplification product, if the target nucleic acid of (i) *B. microti*, and/or (ii) *B. divergens, B. duncani*, and/or *B. venatorum* is present in the sample, with one or more probes; and
   (c) detecting the presence or absence of the amplification product, wherein the presence of the amplification product is indicative of the presence of (i) *B. microti*, and/or (ii) *B. divergens, B. duncani*, and/or *B. venatorum* in the sample, and wherein the absence of the amplification product is indicative of the absence of (i) *B. microti*, and/or (ii) *B. divergens, B. duncani*, and/or *B. venatorum* in the sample, and
   wherein the one or more set of primers and the one or more probes comprise:
      (1) a set of primers for amplification of *B. microti* comprising:
         a primer comprising the nucleic acid sequence of SEQ ID NO:1, or a complement thereof, and
         a primer comprising the nucleic acid sequence of SEQ ID NO:3, or a complement thereof, and
         a probe for hybridizing to the amplification product of *B. microti* comprising the nucleic acid sequence of SEQ ID NO:2, or a complement thereof; and/or
      (2) a set of primers for amplification of *B. divergens, B. duncani*, and/or *B. venatorum* comprising:
         a primer comprising the nucleic acid sequence of SEQ ID NO:4 or a complement thereof, and
         one or more primers compromising the nucleic acid sequence(s) of SEQ ID NO:6 SEQ ID NO:7 or a combination of SEQ ID NOs:6 and 7, or a complement thereof; and
         probe for hybridizing to the amplification product of *B. divergens, B. duncani*, and/or *B. venatorum* comprising the nucleic acid sequence of SEQ ID NO:5, or a complement thereof.

2. The method of claim 1, wherein the sample is a biological sample.

3. The method of claim 2, wherein the biological sample is whole blood, respiratory specimens, urine, fecal specimens, blood specimens, plasma, dermal swabs, nasal swabs, wound swabs, blood cultures, skin, or soft tissue infections.

4. The method of claim 3, wherein the biological sample is whole blood.

5. The method of claim 1, wherein the hybridization step comprises contacting the amplification product with the one or more probes, wherein the one or more probes is labeled with a donor fluorescent moiety and a corresponding acceptor moiety; and the detecting step comprises detecting the presence or absence of fluorescent resonance energy transfer (FRET) between the donor fluorescent moiety and the acceptor moiety of the one or more probes, wherein the presence or absence of fluorescence is indicative of the presence or absence of Babesia in the sample.

\* \* \* \* \*